United States Patent
Capela et al.

(10) Patent No.: US 10,400,214 B2
(45) Date of Patent: Sep. 3, 2019

(54) TARGET POPULATIONS OF OLIGODENDROCYTE PRECURSOR CELLS AND METHODS OF MAKING AND USING SAME

(71) Applicant: BOCO Silicon Valley, Inc., Palo Alto, CA (US)

(72) Inventors: Alexandra Capela, Mountain View, CA (US); Nobuko Uchida, Palo Alto, CA (US)

(73) Assignee: BOCO SILICON VALLEY, INC., Palo Alto, CA (US)

( * ) Notice: Subject to any disclaimer, the term of this patent is extended or adjusted under 35 U.S.C. 154(b) by 0 days.

(21) Appl. No.: 15/816,323

(22) Filed: Nov. 17, 2017

(65) Prior Publication Data

US 2018/0187148 A1  Jul. 5, 2018

Related U.S. Application Data

(62) Division of application No. 12/646,228, filed on Dec. 23, 2009, now abandoned.

(60) Provisional application No. 61/140,410, filed on Dec. 23, 2008.

(51) Int. Cl.
C12N 5/079 (2010.01)

(52) U.S. Cl.
CPC ...... *C12N 5/0622* (2013.01); *C12N 2501/105* (2013.01); *C12N 2501/115* (2013.01); *C12N 2501/135* (2013.01)

(58) Field of Classification Search
CPC .................................................. C12N 5/0622
See application file for complete search history.

(56) References Cited

U.S. PATENT DOCUMENTS

| | | |
|---|---|---|
| 4,352,883 A | 10/1982 | Lim |
| 4,353,888 A | 10/1982 | Sefton |
| 4,470,461 A | 9/1984 | Stapp |
| 4,753,635 A | 6/1988 | Sagen et al. |
| 4,968,733 A | 11/1990 | Wechs |
| 4,976,859 A | 12/1990 | Wechs |
| 4,980,174 A | 12/1990 | Sagen et al. |
| 5,084,350 A | 1/1992 | Chang et al. |
| 5,122,464 A | 6/1992 | Wilson |
| 5,158,881 A | 10/1992 | Aebischer et al. |
| 5,166,065 A | 10/1992 | Caruthers et al. |
| 5,175,103 A | 10/1992 | Aebischer et al. |
| 5,182,111 A | 1/1993 | Aebischer et al. |
| 5,284,761 A | 2/1994 | Aebischer et al. |
| 5,356,807 A | 10/1994 | Blass et al. |
| 5,411,883 A | 5/1995 | Boss et al. |
| 5,453,357 A | 9/1995 | Hogan |
| 5,589,376 A | 8/1996 | Goelz et al. |
| 5,580,777 A | 12/1996 | Bernard et al. |
| 5,612,211 A | 3/1997 | Wilson et al. |
| 5,672,499 A | 3/1997 | Wilson et al. |
| 5,618,531 A | 4/1997 | Cherksey |
| 5,688,692 A | 4/1997 | Cherksey |
| 5,690,926 A | 11/1997 | Hogan |
| 5,750,376 A | 5/1998 | Weiss et al. |
| 5,753,505 A | 5/1998 | Luskin |
| 5,753,506 A * | 5/1998 | Johe ............... C12N 5/0623 435/325 |
| 5,800,828 A | 9/1998 | Dionne et al. |
| 5,830,651 A | 11/1998 | Cauley et al. |
| 5,843,780 A | 12/1998 | Thomson |
| 5,851,832 A | 12/1998 | Weiss et al. |
| 5,968,829 A | 10/1999 | Carpenter |
| 5,980,885 A | 11/1999 | Weiss et al. |
| 6,200,806 B1 | 3/2001 | Thomson |
| 6,251,669 B1 | 6/2001 | Luskin |
| 6,294,346 B1 | 9/2001 | Weiss et al. |
| 6,361,996 B1 | 3/2002 | Rao et al. |
| 6,497,872 B1 | 12/2002 | Weiss et al. |
| 6,498,018 B1 | 12/2002 | Carpenter |
| 6,642,048 B2 | 11/2003 | Xu et al. |
| 6,734,015 B1 | 5/2004 | Rao et al. |
| 6,777,233 B2 | 8/2004 | Carpenter |
| 6,787,353 B1 | 9/2004 | Rao et al. |
| 6,800,480 B1 | 10/2004 | Bodnar et al. |
| 6,812,027 B2 | 11/2004 | Goldman et al. |
| 6,852,532 B2 | 2/2005 | Mayer-Proschell et al. |
| 7,166,277 B1 | 2/2007 | Weiss et al. |

(Continued)

FOREIGN PATENT DOCUMENTS

| | | |
|---|---|---|
| EP | 0 233 838 A2 | 8/1987 |
| EP | 0 338 841 A1 | 10/1989 |

(Continued)

OTHER PUBLICATIONS

Anchan, R.M., et al. (Jun. 1991). "EGF and TGF-α Stimulate Retinal Neuroepithelial Cell Proliferation In Vitro," *Neuron* 6:923-936.

Ahmadab, I., et al. (1999). "In Vitro Analysis of a Mammalian Retinal Progenitor that Gives Rise to Neurons and Glia," *Brain Res.* 831:1-10.

Akerud, P. et al. (2001) "Neuroprotection through Delivery of Glial Cell Line-Derived Neurotrophic Factor by Neural Stem Cells in a Mouse Model of Parkinson's Disease," *The Journal of Neuroscience* 21:8108-8118.

Akiyama, Y. et al. (2001). "Transplantation Of Clonal Neural Precursor Cells Derived From Adult Human Brain Establishes Functional Peripheral Myelin In The Rat Spinal Cord," *Exp Neurol* 167(1):27-39.

(Continued)

*Primary Examiner* — Robert C Hayes
(74) *Attorney, Agent, or Firm* — Morrison & Foerster LLP

(57) ABSTRACT

This application provides for enriched target populations oligodendrocyte precursor cells (OPCs) that can differentiate into oligodendrocytes. The target OPCs may be expanded and optionally subjected to conditions to induce their differentiation into oligodendrocytes. The target OPCs and their progeny are useful for the treatment of disease associated with demyelination of central nervous system axons.

13 Claims, 3 Drawing Sheets

(56) References Cited

U.S. PATENT DOCUMENTS

| | | | |
|---|---|---|---|
| 7,211,434 | B2 | 5/2007 | Van Der Kooy et al. |
| 7,531,354 | B2 | 5/2009 | Stice et al. |
| 7,968,337 | B2 | 6/2011 | Bruestle |
| 8,785,187 | B2 | 7/2014 | Conti et al. |
| 9,309,495 | B2 | 4/2016 | Conti et al. |
| 9,709,553 | B2 | 7/2017 | Goldman et al. |
| 2001/0044122 | A1 | 11/2001 | Buck et al. |
| 2002/0031792 | A1 | 3/2002 | Uchida et al. |
| 2002/0064873 | A1 | 5/2002 | Renji et al. |
| 2002/0068045 | A1 | 6/2002 | Reubinoff et al. |
| 2003/0008392 | A1 | 1/2003 | Thomson |
| 2003/0032181 | A1 | 2/2003 | Weiss et al. |
| 2003/0059414 | A1 | 3/2003 | Ho et al. |
| 2003/0211087 | A1 | 11/2003 | Goldman |
| 2004/0071672 | A1 | 4/2004 | Hogan |
| 2004/0107454 | A1 | 6/2004 | Wheeler et al. |
| 2006/0014281 | A1 | 1/2006 | Conti et al. |
| 2010/0086998 | A1 | 4/2010 | Buck et al. |
| 2010/0158878 | A1 | 6/2010 | Capela et al. |
| 2014/0370596 | A1 | 12/2014 | Conti et al. |

FOREIGN PATENT DOCUMENTS

| | | |
|---|---|---|
| EP | 1 489 163 A1 | 12/2004 |
| EP | 3 000 877 A1 | 3/2016 |
| JP | H1509592 A | 9/1998 |
| JP | 2001-526884 A | 12/2001 |
| JP | 2002-34580 A | 2/2002 |
| WO | WO-1989/03872 A1 | 5/1989 |
| WO | WO-1990/04019 A1 | 4/1990 |
| WO | WO-1990/06757 A1 | 6/1990 |
| WO | WO-1990/07380 A2 | 7/1990 |
| WO | WO-1990/07380 A3 | 7/1990 |
| WO | WO-1991/02003 A1 | 2/1991 |
| WO | WO-1991/09936 A1 | 7/1991 |
| WO | WO-1991/17242 A1 | 11/1991 |
| WO | WO-1992/19195 A1 | 11/1992 |
| WO | WO-1993/01275 A1 | 1/1993 |
| WO | WO-1993/09802 A2 | 5/1993 |
| WO | WO-1994/03199 A1 | 2/1994 |
| WO | WO-1994/09119 A1 | 4/1994 |
| WO | WO-1994/10292 A1 | 5/1994 |
| WO | WO-1994/16718 A1 | 8/1994 |
| WO | WO-1995/05452 A2 | 2/1995 |
| WO | WO-1995/05452 A3 | 2/1995 |
| WO | WO-1996/15226 A1 | 5/1996 |
| WO | WO-1996/26782 A2 | 9/1996 |
| WO | WO-1996/26782 A3 | 9/1996 |
| WO | WO-2000/17323 A1 | 3/2000 |
| WO | WO-2001/30981 A1 | 5/2001 |
| WO | WO-2001/42421 A2 | 6/2001 |
| WO | WO-2001/42421 A3 | 6/2001 |
| WO | WO-2001/88104 A2 | 11/2001 |
| WO | WO-2001/88104 A3 | 11/2001 |
| WO | WO-2003/008566 A1 | 1/2003 |
| WO | WO-2003/097812 A2 | 11/2003 |
| WO | WO-2003/097812 A3 | 11/2003 |
| WO | WO-2003/104444 A1 | 12/2003 |
| WO | WO-2004/050865 A1 | 6/2004 |
| WO | WO-2005/012318 A2 | 2/2005 |
| WO | WO-2005/012318 A3 | 2/2005 |
| WO | WO-2005/076845 A2 | 8/2005 |
| WO | WO-2005/076845 A3 | 8/2005 |
| WO | WO-2006/044204 A2 | 4/2006 |
| WO | WO-2006/044204 A3 | 4/2006 |
| WO | WO-2008/028531 A1 | 3/2008 |
| WO | WO-2015/073867 A1 | 5/2015 |

OTHER PUBLICATIONS

Almazan, G., et al. (1985). "Epidermal Growth Factor and Bovine Growth Hormone Stimulate Differentiation and Myelination of Brain Cell Aggregates in Culture," *Developmental Brain Research* 21:257-264.

Andres, F. (1989). "Removal and Reimplantation of the Parietal Cortex of Mice During the First Nine Days of Life: Consequences for the Barrelfield," *Journal of Neural Transplantation* 1:11-22.

Baetge, E.E., et al. (1993). "Neural Stem Cells for CNS Transplantation," *Annals of the New York Academy of Sciences* 695:285-291.

Bakay, R.A.E. et al. (1990). Preliminary Report on Adrenal-Brian Transplantation for Parkinsonism In Man, *Stereotact Funct. Neurosurg.* 55:312-323.

Bartlett, P.F., et al. (May 1988). "Immortalization of Mouse Neural Precursor Cells by the c-myc Oncogene," *Proc. Natl. Acad. Sci. USA* 85:3255-3259.

Baumann, N. et al. (Apr. 1, 2001). "Biology Of Oligodendrocyte And Myelin In The Mammalian Central Nervous System," *Physiological Reviews* 81(2):871-927.

Bayer, S. (1985). "Neuron Production in the Hippocampus and Olfactory Bulb of the Adult Rat Brain: Addition or Replacement?" *Annals of the New York Academy of Sciences* 457:163-172.

Bazan, E. et al. (Oct. 2004). "In vitro and in vivo Characterization of Neural Stem Cells," *Histology and Histopathology* 19(4):1261-1275.

Ben-Hur, T. et al. (Oct. 2008). "Prospects of Cell Therapy for Disorders of Myelin," *Annals of the New York Academy of Sciences* 1142:218-249.

Berg, D.T. et al. (Jan. 1991)."Viral Transformation Increases Vitamin K-Dependent γ-Carboxylation of Glutamate." *Exp. Cell Res.* 192(1):32-40.

Bernard, O. et al. (1989). "Role of the c-myc and the N-myc Proto-Oncogenes in the Immortalization of Neural Precursors," *Journal of Neuroscience Research*, Alan R. Liss, Inc. United States, 24:9-20.

Bjorklund, A. et al. (1985). "Neural Grafting in Animal Models of Neurodegenerative Diseases," *Annals of the New York Academy of Sciences* 457:53-81.

Blakemore, W.F. et al. (1988). "Extensive Oligodendrocyte Remyelination Following Injection of Cultured Central Nervous System Cells Into Demyelinating Lesions in Adult Central Nervous System," *Dev. Neurosci.* 10:1-11.

Bossart, E. et al. (Nov.-Dec. 1989). "Epidermal Growth Factor Stimulates Colony Formation and Non-Neuronal Marker Protein Expression by Human Neuroblastoma in Methylcellulose Culture," *Anticancer Research* 9: 1497-1504. Abstract Only.

Bouvier, M.M. et al. (Nov. 1995). "Basic Fibroblast Growth Factor Increases Division and Delays Differentiation of Dopamine Precursors in vitro," *Journal of Neuroscience* 15(11):7141-7149.

Boyles, J. K., et al. (Oct. 15, 1990). "Accumulation of Apolipoproteins in the Regenerating and Remyelinating Mammalian Peripheral Nerve," *The Journal of Biological Chemistry* 265(29):17805-17815.

Bray, G.M. (1990). "Neural Transplantation," *Current Opinion in Neurology and Neurosurgery* 3:926-933.

Bredesen, D.E. et al. (1990). "Neural Transplantation Using Temperature-Sensitive Immortalized Neural Cell: A Preliminary Report," *Annals of Neurology* 27:205-207.

Brickman, Y.G. et al. (Oct. 20, 1995). "Heparan Sulfates Mediate the Binding of Basic Fibroblast Growth Factor to a Specific Receptor on Neural Precursor Cells," *The Journal of Biological Chemistry* 270(42):24941-24948.

Brüstle, O. et al. (Nov. 1998). "Chimeric Brains Generated by Intraventricular Transplantation of Fetal Human Brain Cells Into Embryonic Rats," *Nature Biotechnology* 16:1040-1044.

Calof, A.L. et al. (Jul. 1989). "Analysis of Neurogenesis in a Mammalian Neuroepithelium: Proliferation and Differentiation of an Olfactory Neuron Precursor In Vitro," *Neuron* 3:115-127.

Calof, A.L. et al. (1991). "Regulation of Neurogenesis and Neuronal Differentiation in Primary and Immortalized Cells from Mouse Olfactory Epithelium," *J. Cell Biology* pp. 249-276.

Cattaneo, E. et al., (Aug. 1991). "Identifying and manipulating neuronal stem cells," *Trends in Neurosciences* 14(8):338-340.

(56) References Cited

OTHER PUBLICATIONS

Cattaneo, E. et al. (Oct. 25, 1990). "Proliferation and Differentiation of Neuronal Stem Cells Regulated by Nerve Growth Factor," *Nature* 347:762-765.

Cattaneo, E. et al. (1996). "Non-virally Mediated Gene Transfer into Human Central Nervous System Precursor Cells," *Molecular Brain Research* 42: 161-166.

Cepko, C.L. (1989). "Immortalization of Neural Cells via Retrovirus-Mediated Oncogene Transduction," *Ann. Rev. Neurosci.* 12:47-65.

Chalmers-Redman, R.M.E. et al. (1997). "In vitro Propagation and Inducible Differentiation of Multipotential Progenitor Cells from Human Fetal Brain," *Neuroscience* 76(2):1121-1128.

Chu, M.S. et al. (Apr. 1, 2006). "Signalling Pathway In The Induction of Neurite Outgrowth in Human Mesenchymal Stem Cells," *Cellular Signalling*, Elsevier Science Ltd. 18(4):519-530.

Citri, A. et al. (Jul. 2006). "EGF-ERBB Signalling: Towards the System Level," *Nature Reviews, Molecular Cell Biology* 7:505-516.

Conti, L. et al. (Sep. 2005). "Niche-independent symmetrical self-renewal of a mammalian tissue stem cell," *PLOS Biology*, Article No. E283 3(9):1594-1606.

Cortez, S.C. et al. (Mar. 1989). "Experimental Fluid Percussion Brain Injury: Vascular Disruption and Neuronal and Glial Alterations," *Brain Research* 482:271-282.

Cotter, T. et al. (May-Jun. 1992). "The Induction of Apoptosis by Chemotherapeutic Agents Occurs in All Phases of the Cell Cycle," *Anticancer Research* 12(3):773-780. Abstract Only.

Dahlstrand, J. et al. (1995). "Nestin mRNA Expression Correlates with the Central Nervous System Progenitor Cell State in Many, But Not All, Regions of Developing Central Nervous System," *Developmental Brain Research* 84:109-129.

Date, I., et al. (1990). "MPTP-treated Young Mice but not Aging Mice Show Partial Recovery of the Nigrostriatal Dopaminergic System by Stereotaxic Injection of Acidic Fibroblast Growth Factor (aFGF)," *Brain Research* 526:156-160.

Deloulme, J.C. et al. (1991). "Establishment of Pure Neuronal Cultures from Fetal Rat Spinal Cord and Proliferation of the Neuronal Precursor Cells in the Presence of Fibroblast Growth Factor," *Journal of Neuroscience Research* 29:499-509.

Doetsch, F., et al. (Dec. 19, 2002). "EGF Converts Transit-Amplifying Neurogenic Precursors in the Adult Brain into Multipotent Stem Cells," *Neuron* 36:1021-1034.

Drago, J., et al. (Mar. 1991). "Fibroblast Growth Factor-mediated Proliferation of Central Nervous System Precursors Depends on Endogenous Production of Insulinlike Growth Factor I," *Proc. Natl. Acad. Sci. USA* 88:2199-2203.

Duittoz, A.H. et al. (2001). "Primary Culture of Neural Precursors from the Ovine Central Nervous System (CNS)," *J. Neurosci. Meth.* 107:131-140.

Dunnett, S.B., et al. (Jul. 1983). "Dopamine-rich Transplants in Experimental Parkinsonism," *Trends in Neurosciences* 6:266-270.

Emerich, D.F. et al. (1992). "Behavioral Effects of Neural Transplantation," *Cell Transplantation* 1(6):401-427. Abstract Only.

Ernsberger, U. et al. (Mar. 1989). "Proliferation and Differentiation of Embryonic Chick Sympathetic Neurons: Effects of Ciliary Neurotrophic Factor," *Neuron* 2:1275-1284.

Evrard, C. et al. (Apr. 1990). "Immortalization of Bipotential and Plastic Glio-Neuronal Precursor Cells," *Proc. Natl. Acad. Sci. USA* 87:3062-3056.

Faaland, C.A., et al. (May 1991). "Rapid Uptake of Tyrphostin into A431 Human Epidermoid Cells Is Followed by Delayed inhibition of Epidermal Growth Factor (EGF)-Stimulated EGF Receptor Tyrosine Kinase Activity," *Molecular and Cellular Biology* 11(5):2697-2703.

Federoff, H.J. et al. (Mar. 1992). "Expression of Nerve Growth Factor In Vivo from a Defective Herpes Simplex Virus 1 Vector Prevents Effects of Axotomy on Sympathetic Ganglia," *Proc. Natl. Acad. Sci. USA* 89:1636-1640.

Ferguson, I.A et al. (1991). "Fibroblast Growth Factor Receptor-Bearing Neurons in the CNS: Identification by Receptor-mediated Retrograde Transport," *The Journal of Comparative Neurology* 313:693-706.

Ferrari, G. et al. (May 1989). "Basic Fibroblast Growth Factor Promotes the Survival and Development of Mesencephalic Neurons n Culture," *Developmental Biology* 133(1):140-147. Abstract Only.

Flax, J.D. et al. (Nov. 1998) "Engraftable Human Neural Stem Cells Respond to Developmental Cues, Replace Neurons, and Express Foreign Genes," *Nature Biotechnology* 16:1033-1039.

Franklin, M., et al. (May 1991). "Transplanted Type-1 Astrocytes Facilitate Repair of Demyelination Lesions by h Oligodendrocytes in Adult Rat Spinal Cord," *Neuropathol. Appl. Neurobiol.* 20(5):420-430. Abstract Only.

Frederiksen, K. et al. (Apr. 1988). "Proliferation and Differentiation of Rat Neuroepithelial Precursor Cells In Vivo," *The Journal of Neurosciences* 8:1144-1151.

Frederiksen, K., et al. (Aug. 1988). "Immortalization of Precursor Cells from the Mammalian CNS," *Neuron* 1:439-448.

Freed, C.R., et al. (May 1990). "Transplantation of Human Fetal Dopamine Cells for Parkinson's Disease. Results at 1 Year," *Arch. Neural.* 47:505-512.

Fricker, R.A. et al. (Jul. 15, 1999). "Site-specific Migration and Neuronal Differentiation of Human Neural Progenitor Cells after Transplantation in the Adult Rat Brain," *The Journal of Neuroscience* 19(14):5990-6005.

Friedmann, T. (Jun. 1994). "Gene Therapy for Neurological Disorders," *Trends in Genetics* 10(6):210-214.

Fults, D., et al. (May 1992). "Establishment and Characterization of a Human Primitive Neuroectodermal Tumor Cell Line from the Cerebral Hemisphere," *Journal of Neuropathology and Experimental Neurology* 51(3):272-280.

Gard, A.L. et al. (1995). "Oligodendroblasts Distinguished From O-2A Glial Progenitors By Surface Phenotype ($O4^+GalC^-$) And Repsonse To Cyokines Using Signal Transducer LIPFβ," *Developmental Biology* 167:596-608.

Geller, A.I. et al. (Sep. 23, 1988). "A Defective HSV-1 Vector Expresses *Escherichia coli* β—Galactosidase in Cultured Peripheral Neurons," *Science* 241:1667-1669.

Gensburger, C., et al. (Jun. 1987). "Brain Basic Fibroblast Growth Factor Stimulates the Proliferation of Rat Neuronal Precursor Cells In Vitro," *FEBS Lett* 217(1):1-5.

Godfraind, C. et al. (Nov. 1989). "In Vivo Analysis of Glial Cell Phenotypes During a Viral Demyelinating Disease in Mice," *The Journal of Cell Biology* 109:2405-2416.

Goetz, C.G. et al. (1991). "United Parkinson Foundation Neurotransplantation Registry on Adrenal Medullary Transplants: Presurgical, and 1- and 2-Year Follow-up," *Neurology* 41:1719-1722.

Gregg, C. et al. (Dec. 17, 2003). "Generation of Functional Radial Glial Cells by Embryonic and Adult Forebrain Neural Stem Cells," *J. Neurosci.* 23(37):11581-11601.

Gritti, A. et al. (May 1, 1999). "Epidermal and Fibroblast Growth Factors Behave As Mitogenic Regulators for a Single Multipotent Stem Cell-Like Population From the Subventricular Region of the Adult Mouse Forebrain," *Journal of Neuroscience* 19(9):3287-3297.

Gritti, A., et al. (Jan. 15, 2002). "Multipotentneural Stem Cells Reside in the Rostral Extension and Olfactory Bulb of Adult Rodents," *The J. of Neuroscience* 22(2):437-445.

Groves, A.K., et al. (Apr. 1, 1993). "Repair of Demyelinated Lesions by Transplantation of Purified O-2A Progenitor Cells," *Nature* 362:453-455.

Guentert-Lauber, et al. (1985). "Responsiveness of Astrocytes in Serum-Free Aggregate Cultures to Epidermal Growth Factor: Dependence on the Cell Cycle and the Epidermal Growth Factor Concentration," *Dev. Neurosci.* 7:286-295.

Hall, P.A. et al. (1989). "Stem Cells: the Generation and Maintenance of Cellular Diversity," *Development* 106:619-633.

Hammang, J.P. et al. (1994). "Transplantation of Epidermal Growth Factor-Responsive Neural Stem Cell Progeny into the Murine Central Nervous System," *Methods in Neurosciences* 21:281-293.

(56) References Cited

OTHER PUBLICATIONS

Hammang, J.P. et al. (1997). "Myelination Following Transplantation of EGF-Responsive Neural Stem Cells into a Myelin-Deficient Environment," *Experimental Neurology* 147:84-95.

Heikkila, R.E. et al. (1987). "The Use of the MPTP-Treated Mouse as an Animal Model of Parkinsonism," *Can. J. Neural. Sci.* 14:436-440.

Heins, N. et al. (Apr. 2002, e-pub. Mar. 18, 2002). "Glial Cells Generate Neurons: The Role of the Transcription Factor Pax6," *Nat. Neurosci.* 5(4):308-315.

Hockfield, S. et al. (Dec. 1985). "Identification of Major Cell Classes in the Developing Mammalian Nervous System," *The Journal of Neuroscience* 5(12):3310-3328.

Hodgson, C.P. (1995). "Patent Update: Biologicals & Immunologicals: Advances in Vector Systems for Gene Therapy," *Exp. Opin. Ther. Patents* 5(5):459-468.

Hoffman, D., et al. (1993). "Transplantation of a Polymer-Encapsulated Cell Line Genetically Engineered to Release NGF," *Experimental Neurology* 122:100-106.

Hollenberg, M.D. et al. (Oct. 1973). "Epidermal Growth Factor: Receptors in Human Fibroblasts and Modulation of Action by Cholera Toxin," *Proc. Natl. Acad. Sci. USA* 70(10):2964-2968.

Hunter, S.F. et al. (Jul. 1, 1990). "Growth Factor Responses Of Enriched Bipotential Glial Progenitors," *Developmental Brain Res.* 54(2):235-248.

Hurtig, H. et al. (1989). "Postmortem Analysis of Adrenal-Medullato-Caudate Autograft in a Patient with Parkinson's Disease," *Annals of Neurology* 25(6):607-614.

Isacson, O. et al. (1989). "A Primate Model of Huntington's Disease: Cross-Species Implantation of Striatal Precursor Cells to the Excitotoxically Lesioned Baboon Caudate-Putamen," *Exp. Brain Res.* 75:213-220.

Jackowski, A. (1995). "Neural Injury Repair: Hope for the Future as Barriers to Effective CNS Regeneration become Clearer," *British Journal of Neurosurgery* 9:303-317.

Jänisch, V.W. et al. (1992). "Expression of Immunohistochemical Differentiation Markers in Normal and Transformed Neoplastic Neuroectodermal Stem Cells," *Acta Histochemica* 42:139-147. Abstract Only.

Jiao, S. et al. (1992). "Intracerebral Transplants of Primary Muscle Cells: A Potential 'Platform' for Transgene Expression in the Brain," *Brain Research* 575:143-147.

Kamholz, J. et al. (Jul. 1996). "Identification of Three Forms of Human Myelin Basic Protein by cDNA Cloning," *Proc. Natl. Acad. Sci. USA* 83:4962-4966.

Kaplan, M.S. (1981). "Neurogenesis in the 3-Month-Old Rat Visual Cortex," *The Journal of Comparative Neurology* 195:323-338.

Kawaja, M.D. et al. (Jul. 1992). "Somatic Gene Transfer of Nerve Growth Factor Promotes the Survival of Axotomized Septa! Neurons and the Regeneration of Their Axons in Adult Rats," *The Journal of Neuroscience* 12(7):2849-2864.

Kesslak, J.P. et al. (1986). "Adult and Embryonic Frontal Cortex Transplants After Frontal Cortex Ablation Enhance Recovery on a Reinforced Alternation Task," *Experimental Neurology* 94:615-626.

Kojima, A. et al. (Aug. 2000). "Epidermal Growth Factor and Fibroblast Growth Factor 2 Cause Proliferation of Ependymal Precursor Cells in the Adult Rat Spinal Cord in Vivo," *J. Neuropathol. Exp. Neurol.* 59(3):687-697.

Kordower, J.H. et al. (1992). "Neurogenesis of the Amygdaloid Nuclear Complex in the Rhesus Monkey," *Developmental Brian Research* 68:9-15.

Korr, H., et al. (1973). "Autoradiographic Investigations of Glial Proliferation in the Brain of Adult Mice. I. The DNA synthesis phase of neuroglia and endothelial cells," *J. Comp. Neur.* 150:169-175.

Kumar, S. et al. (Jun. 30, 1992). "Identification of a Set of Genes with Developmentally Down-Regulated Expression in the Mouse Brain," *Biochemical and Biophysical Research Communications* 185(3):1155-1161.

Latorre, A. et al. (Feb. 16, 2016). "Modified RNAs in CRISPR/Cas9: An Old Trick Works Again," *Angewandte Chemie International Edition* 55(11):3549-3550.

Lendahl, U. et al. (Feb. 23, 1990). "CNS Stem Cells Express a New Class of Intermediate Filament Protein," *Cell* 60:585-595.

Lin, L.-F.H. et al. (May 21, 1993). "GDNF: A Glial Cell Line-Derived Neurotrophic Factor for Midbrain Dopaminergic Neurons," *Science* 260:1130-1132.

Lindvall, O. et al. (Jun. 1989). "Human Fetal Dopamine Neurons Grafted into the Striatum in Two Patients with Severe Parkinson's Disease A Detailed Account of Methodology and a 6-month Follow-up," *Arch. Neural.* 46:615-631.

Lindvall, O. et al. (Feb. 2, 1990). "Grafts of Fetal Dopamine Neurons Survive and Improve Motor Function in Parkinson's Disease," *Science* 247(4942): 574-577.

Liour, S.S. et al. (Apr. 2003). "Differentiation of Radial Glia-Like Cells From Embryonic Stem Cells," *Glia* 42:109-117.

Lo, L.-C., et al. (1991). "V-myc Immortalization of Early Rat Neural Crest Cells Yields a Clonal Cell Line Which Generates Both Glial and Adrenergic Progenitor Cells," *Developmental Biology* 145:139-153.

Lois, C. et al. (May 20, 1994). "Long-Distance Neuronal Migration in the Adult Mammalian Brian," *Science* 264:1145-1148.

Lubetzki, C., et al. (1990). "Gene Transfer of Rat Mature Oligodendrocytes and Glial Progenitor Cells with the Lacz Gene," *Annals of the New York Academy of Sciences* 605: 66-70.

Luskin, M.B., et al. (1994). "Rate and Pattern of Migration of Lineally-Related Olfactory Bulb Interneurons Generated Postnatally in the Subventricular Zone of the Rat," *Chemical Senses* 19(6):695-714.

Mantel, C., et al. (1995). "Macrophage Inflammatory Protein-1 α Enhances Growth Factor-Stimulated Phosphatidylcholine Metabolism and Increases cAMP Levels in the Human Growth Factor-Dependent Cell Line M07e, Events Associated with Growth Suppression," *The Journal of Immunology* 154:2342-2350.

Marchal-Victorion, S. et al. (Sep. 2003). "The Human NTERA2 Neural Cell Line Generates Neurons on Growth Under Neural Stem Cell Conditions and Exhibits Characteristics of Radial Glial Cells," *Mol. Cell Neurosci.* 24(1):198-213.

Maric, D. et al. (Jan. 1, 2003). "Prospective Cell Sorting Of Embryonic Rat Neural Stem Cells And Neuronal And Glial Progenitors Reveals Selective Effects of Basic Fibroblast Growth Factor And Epidermal Growth Factor On Self-Renewal and Differentiation," *Journal of Neuroscience* 23(1):240-251.

Masters, B.A. et al. (1991). "Insulin-like Growth Factor I(IGF-1) Receptors and IGF-1 Action in Oligodendrocytes from Rat Brains," *Regulatory Peptides* 33:117-131.

McDermott, A.M. et al. (1992). "Thyrotropin Releasing Hormone (TRH) and a Degradation Stabilized Analogue (RX77368) Stimulate Phosphoinositide Turnover in Cultured Astrocytes in a Regionally Specific Manner," *Neurochem. Int.* 20(3):307-313.

McKay, R. (Apr. 4, 1997). "Stem Cells in the Central Nervous Systems," *Science* 276:66-71.

McKeon, R.J. et al. (Nov. 1991). "Reduction of Neurite Outgrowth in a Model of Glial Scarring Following CNS Injury is Correlated with the Expression of Inhibitory Molecules on Reactive Astrocytes," *The Journal of Neuroscience* 11(11):3398-3411.

McKinnon, R.D. et al. (Nov. 1990). "FGF Modulates the PDGF-Driven Pathway of Oligodendrocyte Development," *Neuron* 5:603-614.

Mehler, M.F. et al. (Jul. 1999). "Progenitor Cell Biology: Implications for Neural Regeneration," *Arch Neural* 56(7):780-784.

Memberg, S.P. et al. (1995). "Proliferation, Differentitation, and Survival of Rat Sensory Neuron Precursors in vitro Require Specific Trophic Factors," *Molecular and Cellular Neuroscience* 6:323-335.

Merkle, F.T. et al. (Dec. 14, 2004). "Radial Glia Give Rise to Adult Neural Stem Cells in the Subventricular Zone," *Proc. Natl. Acad. Sci. USA* 101(50):17528-17532.

Metcalf, D. (Dec. 1992). "The Hemopoietic Regulators—An Embarrassment of Riches," *BioEssays* 14(12):799-805.

Micci, M-A. et al. (2001). "Neural Stem Cells Express RET, Produce Nitric Oxide, and Survive Transplantation in the Gastrointestinal Tract," *Gastroenterology* 121:757-766.

(56) References Cited

OTHER PUBLICATIONS

Mignone, J.L. et al. (2004). "Neural Stem and Progenitor Cells in Nestin-GFP Transgenic Mice," *J. Comp. Neurol.* 469:311-324.
Milward, E.A. et al. (Dec. 1, 1997). "Isolation and Transplantation Of Multipotential Populations Of Epidermal Growth Factor-Responsive, Neural Progenitor Cells From the Canine Brain," *J. Neurosci Res.* 50(5):862-871.
Monnet-Tschudi, F. et al. (1989). "Influence of Epidermal Growth Factor on the Maturation of Fetal Rat Brain Cells in Aggregate Culture," *Dev. Neurosci.* 11:30-40.
Morest, D.K. et al. (Jul. 2003). "Precursors of Neurons, Neuroglia, and Ependymal Cells in the CNS: What Are They? Where Are They From? How Do They Get Where They Are Going?," *Glia* 43:6-18.
Morrison, R. et al. (Oct. 2, 1987). "Trophic Stimulation of Cultured Neurons from Neonatal Rat Brain by Epidermal Growth Factor," *Science* 238:72-75.
Morshead, C. et al. (Nov. 1994). "Neural Stem Cells in the Adult Mammalian Forebrain: A Relatively Quiescent Subpopulation of Subependymal Cells," *Neuron* 13:1071-1082.
Morshead, C.M. et al. (Jan. 1992). "Postmitotic Death is the Fate of Constitutively Proliferating Cells in the Subependymal Layer of the Adult Mouse Brain," *The Journal of Neuroscience* 12(1):249-256.
Murphy, M. et al. (1990). "Fibroblast Growth Factor Stimulates the Proliferation and Differentiation of Neural Precursor Cells In Vitro," *Journal of Neuroscience Research* 25:463-475.
Mytilineou, C. et al. (1992). "Epidermal Growth Factor-Induced Survival and Proliferation of Neuronal Precursor Cells from Embryonic Rat Mesencephalon," *Neuroscience Letters* 135:62-66.
Nakafuku, M. et al. (Jan. 1993). "Epidermal Growth Factor and Transforming Growth Factor-a can Induce Neuronal Differentiation of Rat Pheochromocytoma PC12 Cells Under Particular Culture Conditions," *FEBS* 315(3):227-232.
Nakayama, T. et al. (Mar. 1, 2004). "Efficient Production of Neural Stem Cells and Neurons From Embryonic Stem Cells," *Neuroreport* 15(3):487-491.
Notter, M.F.D. et al. (1986). "Neuronal Properties of Monkey Adrenal Medulla In Vitro," *Cell Tissue Res.* 244:69-76.
Nurcombe, V. et al. (Apr. 2, 1993). "Developmental Regulation of Neural Response to FGF-1 and FGF-2 by Heparan Sulfate Proteoglycan," *Science* 260:103-106.
Olson, L. (1990). "Grafts and Growth Factors in CNS," *Stereotact. Funct. Neurosurg.* 54:250-267.
Orkin, S.H. et al. (Dec. 7, 1995). "Report and Recommendations of the Panel to Assess the NIH Investment in Research on Gene Therapy," *National Institute of Health*, United States, 37 pages.
Ostenfeld, T. et al. (Sep. 2004), "Requirement for Neurogenesis to Proceed through the Division of Neuronal Progenitors following Differentiation of Epidermal Growth Factor and Fibroblast Growth Factor-2-Responsive Human Neural Stem Cells," *Stem Cells* 22:798-811.
Palella, T.D. et al. (1989). "Expression of Human HPRT mRNA in Brains of Mice Infected with a Recombinant Herpes SimplexVirus-1 Vector," *Gene* 80:137-144.
Pallage, V. et al. (1986). "Long-term Effects of Nerve Growth Factor and Neural Transplants on Behavior of Rats with Medial Septal Lesions," *Brain Research* 386:197-208.
Palmer, A.C. (1991). "Proceedings of the Eighty-first Meeting of the British Neuropathological Society held at the Institute of Psychiatry Jan. 10-11, 1991," *Neuropathology and Applied Neurobiology* 17:239-258.
Palmer, T. D. et al. (Feb. 1991). "Genetically Modified Skin Fibroblasts Persist Long After Transplantation but Gradually Inactivate Introduced Genes," *Proc. Natl. Acad. Sci. USA* 88:1330-1334.
Paterson, J.A. (1983). "Dividing and Newly Produced Cells in the Corpus Callosum of Adult Mouse Cerebrum as Detected by Light Microscopic Radioautography," *Anat. Anz.* 153(2):149-168. Abstract Only.
Perlow, M.J. et al. (May 11, 1979). "Brain Grafts Reduce Motor Abnormalities Produced by Destruction of Nigrostriatal Dopamine System," *Science* 204:643-647.

Pezzoli, G. et al. (1991). "Intraventricular Infusion of Epidermal Growth Factor Restores Dopaminergic Pathway in Hemiparkinsonian Rats," *Movement Disorders* 6(4):281-287.
Pluchino, S. et al. (Apr. 17, 2003). "Injection Of Adult Neurospheres Induces Recovery In A Chronic Model Of Multiple Sclerosis," *Nature* 422(6933):688-694.
Potten, C.S. et al. (1990). "Stem Cells: Attributes, Cycles, Spirals, Pitfalls and Uncertainties Lessons for and from the Crypt," *Development* 110:1001-1020.
Price, J. et al. (1988). "Cell Lineage in the Rat Cerebral Cortex: A Study Using Retroviral-Mediated Gene Transfer," *Development* 104:473-482.
Price, J., et al. (1991). "Cell Lineage in the Cerebral Cortex," *Development Supplement* 2:23-28.
Price, J. et al. (2001). "Neural Stem Cells," *Current Opinion in Neurobiology* 11:564-567.
Pulliam, L. et al. (1988). "A Normal Human Brain Cell Aggregate Model for Neurobiological Studies," *Journal of Neuroscience Research* 21:521-530.
Raff, M.C. et al. (Jun. 2, 1983). "A Glial Progenitor Cell That Develops in vitro Into an Astrocyte or an Oligodendrocyte Depending on Culture Medium," *Nature* 303:390-396.
Rakic, P. (Mar. 1, 1985). "Limits of Neurogenesis in Primates," *Science* 227:1054-1056.
Reh, T.A. et al. (Dec. 1989). "Age of Differentiation Determines Rat Retinal Germinal Cell Phenotype: Induction of Differentiation by Dissociation," *Journal of Neuroscience* 9(12):4179-4189.
Reitze, R.L. et al. (Aug. 16, 2001). "Purification of a Pluripotent Neural Stem Cell from the Adult Mouse Brain," *Nature* 412:736-739.
Renfranz, P.J. et al. (Aug. 23, 1991). "Region-Specific Differentiation of Hippocampal Stem Cell Line HiB5 upon Implantation into the Developing Mammalian Brain," *Cell* 66:713-729.
Reynolds, B.A. et al. (Mar. 27, 1992). "Generation of Neurons and Astrocytes from Isolated Cells of the Adult Mammalian Central Nervous System," *Science* 255:1707-1710.
Reynolds, B.A. et al. (Nov. 1992). "A Multipotent EGF-Responsive Striatal EmbryonicProgenitor Cell Produces Neurons and Astrocytes," *J. Neurosci.* 12(11):4565-4574.
Reynolds, B.A. et al. (1996). "Clonal and Population Analyses Demonstrate That an EGF-Responsive Mammalian Embryonic CNS Precursor Is a Stem Cell," *Develop. Biol.* 175:1-13.
Rezvani, M. et al. (2001). "Modification of Radiation Myelopathy by the Transplantation of Neural Stem Cells in the Rat," *Radiation Research* 156(4):408-412.
Richards, L.J. et al. (Sep. 1992). "De novo Generation of Neuronal Cells from the Adult Mouse Brain," *Proc. Natl. Acad. Sci. USA* 89:8591-8595.
Richardson, W.D. et al. (Apr. 22, 1988). "A Role for Platelet-Derived Growth Factor In Normal Gliogenesis In The Central Nervous System," *Cell* 53(2):309-319.
Ronnett, G.V. et al. (May 4, 1990). "Human Cortical Neuronal Cell Line: Establishment from a Patient with Unilateral Megalencephaly," *Science* 248:603-605.
Rosenberg, M.B. et al. (Dec. 16, 1988). "Grafting Genetically Modified Cells to the Damaged Brain: Restorative Effect of NGF Expression," *Science* 242:1575-1578.
Rossi, F. et al. (May 2002). "Opinion: Neural Stem Cell Therapy for Neurological Diseases: Dreams and Reality," *Nat. Rev. Neurosci* 3(5):401-409.
Rovasio, R.A. et al. (1983, e-pub. Feb. 1, 1983). "Neural Crest Cell Migration: Requirements for Exogenous Fibronectin and High Cell Density," *J. of Cell Biology* 96:462-473.
Rudland, P.S. et al. (Jul. 1974). "Growth Control in Cultured Mouse Fibroblasts: Induction of the Pleiotypic and Mitogenic Responses by a Purified Growth Factor," *Proc. Natl. Acad. Sci. USA* 71(7):2600-2604.
Ryder, E.F. et al. (1990). "Establishment and Characterization of Multipoint Neural Cell Lines Using Retrovirus Vector-Mediated Oncogene Transfer," *Journal of Neurobiology* 21(2):356-375.

(56) References Cited

OTHER PUBLICATIONS

Saneto, R.P. et al. (1998). "Insulin/Insulin-Like Growth Factor I and Other Epigenetic Modulators of Myelin Basic Protein Expression in Isolated Oligodendrocyte Progenitor Cells," *Journal of Neuroscience Research* 21:210-219.

Sensenbrenner, M. et al. (Jan.-Mar. 1994). "Proliferation of Neuronal Precursor Cells from the Central Nervous System in Culture," *Reviews in the Neurosciences* 5(1):43-53. Abstract Only.

Shen, Q. et al. (2004, e-pub. Apr. 1, 2004). "Endothelial Cells Stimulate Self-Renewal and Expand Neurogenesis of Neural Stem Cells," *ScienceMag.*, pp. 19-23.

Smart, I. (1961). "The Subependymal Layer of the Mouse Brain and its Cell Production as Shown by Radioautography after Thymidine-H3 Injection," *The Journal of Comparative Neurology* 116:325-347.

Snyder, E.Y. et al. (Jan. 10, 1992). "Multipotent Neural Cell Lines Can Engraft and Participate in Development of Mouse Cerebellum," *Cell* 68:33-51.

Steinbusch, H.W.M., et al. (1990). "Basic Fibroblast Growth Factor Enhances Survival and Sprouting of Fetal Dopaminergic Cells Implanted in the Denervated Rat Caudate-Putamen: Preliminary Observations," *Progress in Brain Research* 82:81-86.

Stenevi, U. et al. (1974). "Effects of Localized Intracerebral Injections of Nerve Growth Factor on the Regenerative Growth of Lesioned Central Noradrenergic Neurones," *Brain Research* 69:217-234.

Tanigaki, K. et al. (Jan. 2001). "Notch1 and Notch3 Instructively Restrict bFGF-Responsive Multipotent Neural Progenitor Cells to an Astroglial Fate," *Neuron* 29:45-55.

Taupin, P. et al. (Nov. 2000). "FGF-2-Responsive Neural Stem Cell Proliferation Requires CCg, a Novel Autocrine/Paracrine Cofactor," *Neuron* 28:385-397.

Temple, S. (Aug. 10, 1989). "Division and Differentiation of Isolated CNS Blast Cells in Microculture," *Nature* 340:471-473.

Toda, H., et al. (2001). "Grafting Neural Stem Cells Improved the Impaired Spatial Recognition in Ischemic Rats," *Neuroscience Letters* 361:9-12.

Tohyama, T. et al. (Mar. 1992). "Nestin Expression in Embryonic Human Neuroepithelium and in Human Neuroepithelial Tumor Cells," *Laboratory Investigation* 66(3):303-313. Abstract Only.

Travis, J. (Mar. 26, 1993). "The Search for Liver Stem Cells Picks Up," *Science* 259:1829.

Tropepe, V. et al. (Apr. 2001). "Direct Neural Fate Specification from Embryonic Stem Cells: A Primitive Mammalian Neural Stem Cell Stage Acquired through a Default Mechanism," *Neuron* 30:65-78.

Uchida, N. et al. (Dec. 19, 2000). "Direct Isolation of Human Central Nervous System Stem Cells," *Proc. Natl. Acad. Sci. USA* 97(26):14720-14725.

Uchida, N. et al. (Oct. 10, 2012). "Human Neural Stem Cells Induce Functional Myelination in Mice With Severe Dysmyelination," *Sci. Transl. Med.* 4(155):155ra136, 23 pages.

Urnov, F.D. et al. (Sep. 2010). "Genome Editing with Engineering Zinc Finger Nucleases," *Nature Reviews Genetics* 11:636-646.

Van Der Maazen, R. et al. (1991). "Radiosensitivity of Glial Progenitor Cells of the Perinatal and Adult Rat Optic Nerve Studied by an In vitro Clonogenic Assay," *Radiotherapy and Oncology* 20:258-624.

Vescovi, AL. et al. (Nov. 1993). "bFGF Regulates the Proliferative Fate of Unipotent (Neuronal) and Bipotent (Neuronal/Astroglial) EGF-Generated CMS Progenitor Cells," *Neuron* 11:951-966.

Vescovi, A.L. et al. (1999). "Isolation and Cloning of Multipotential Stem Cells From the Embroyonic Human CNS and Establishment of Transplantable Human Neural Stem Cell by Epigenetic Stimulation," *Experimental Neurology* 156:71-83.

Villa, P. et al. (1994). "Synthesis of Specific Proteins in Trophic Factor-Deprived Neurons Undergoing Apoptosis," *J. Neurochem.* 62:1468-1475.

Walsh, C. et al. (Sep. 9, 1988). "Clonally Related Cortical Cells Show Several Migration Patterns," *Science* 241:1342-1345.

Weiss, S. et al. (Apr. 1986). "Synaptogenesis of Cultured Striatal Neurons in Serum-free Medium: A Morphological and Biochemical Study," *Proc. Natl. Acad. Sci. USA* 83:2238-2242.

Weiss, S. et al. (Dec. 1, 1996). "Multipotent CNS Stem Cells Are Present in the Adult Mammalian Spinal Cord and Ventricular Neuroaxis," *The Journal of Neuroscience* 16(23):7599-7609.

Wendt, J.S. et al. (1983). "Regeneration of Rat Hippocampal Fimbria Fibers after Fimbria Transection and Peripheral Nerve or Fetal Hippocampal Implantation," *Experimental Neurology* 79:452-461.

Widner, H. et al. (Nov. 26, 1992). "Bilateral Fetal Mesencephalic Grafting in Two Patients with Parkinsonism Induced by 1-Methyl-4-phenyl-1,2,3,6-tetrahydropyridine (MPTP)," *N. Engl. J. of Med.* 327(22):1556-1563.

Williams, L.R. et al. (Dec. 1986). "Continuous Infusion of Nerve Growth Factor Prevents Basal Forebrain Neuronal Death after Fimbria Fornix Transaction," *Proc. NatL.Acad. Sci. USA* 83:9231-9235.

Winkler, C. et al. (1998). "Incorporation and Glial Differentiation of Mouse EGF-Responsive Neural Progenitor Cells after Transplantation into the Embryonic Rat Brain," *Molecular and Cellular Neuroscience* 11:99-116.

Wolff, J.A. et al. (Nov. 1989). "Grafting Fibroblasts Genetically Modified to Produce L-dopa in a rat Model of Parkinson Disease," *Proc. Natl. Acad. Sci. USA* 86:9011-9014.

Wolswijk, G. et al. (1989). "Identification of an Adult-Specific Glial Progenitor Cell," *Development* 105:387-400.

Yandava, B.D. et al. (Jun. 1999) "'Global' Cell Replacement Is Feasible Via Neural Stem Cell Transplantation: Evidence From the Dysmyelinated Shiverer Mouse Brain," *Proc. Natl. Acad. Sci. USA* 96(12):7029-7034.

Ying, Q-L et al. (Feb. 2003). "Conversion of Embryonic Stem Cells Into Neuroectodermal Precursors in Adherent Monoculture," *Nature Biotechnology* 21(2):183-186.

Ying, Q-L. et al. (2003). "Defined Conditions for Neural Commitment and Differntiation," *Methods in Enzymology* 365:327-341.

Zhang, S.-U. et al. (Mar. 1999). "Adult Brain Retains The Potential To Generate Oligodendroglial Progenitors With Extensive Myelination Capacity," *Proc. Natl. Acad. Sci. USA* 96(7):4089-4094.

Zhou, F.C. et al. (1998). "Long-term Nonpassaged EGF-Responsive Neural Precursor Cells Are Stem Cells," *Wound Rep. Reg.* 6:337-348.

Zigova, T. et al. (Nov. 1998). "The Rising Star of Neural Stem Cell Research," *Nature Biotechnology* 16:1007-1008.

Decision To Grant, dated Nov. 4, 2016, in connection with European Patent Application No. 09795884.7, 2 pages.

Espacenet English Language Abstract of Japanese Patent Application Publication No. 2002-34580, published Feb. 5, 2002.

European Search Report for EP16201264.5 dated Apr. 7, 2017, 8 pages.

European Office Action for Application 15187447.3 dated Dec. 1, 2016, 9 pages.

Extended European Search Report for EP15187477.3 dated Feb. 8, 2016.

Examination Report, dated Mar. 4, 2013, in connection with European Patent Application No. 09795884.7, 5 pages.

Examination Report, dated May 30, 2014, in connection with European Patent Application No. 09795884.7, 4 pages.

Final Office Action for U.S. Appl. No. 12/646,228 dated Apr. 17, 2017 and filed Dec. 23, 2009.

International Preliminary Report On Patentability, dated Jun. 29, 2011, for Application No. PCT/US2009/069385, filed Dec. 23, 2009, 6 pages.

International Search Report, Application No. PCT/US2009/069385, dated Feb. 24, 2009, 4 pages.

International Preliminary Report On Patentability, Application No. PCT/GB2005/002289, dated Oct. 30, 2006, filed Jul. 9, 2005, 16 pages.

Letter/Written Disclosure Of The Supplemental Information Disclosure Statement for the above referenced application filed herewith on Jan. 13, 2017, 2 pages.

(56) References Cited

OTHER PUBLICATIONS

Response, dated Sep. 12, 2013, to Examination Report, dated Mar. 4, 2013, in connection with European Patent Application No. 09795884.7, 17 pages.

Response, dated Oct. 2, 2014, to Examination Report, dated May 30, 2014, in connection with European Patent Application No. 09795884.7, 29 pages.

Summons to Attend Oral Proceedings Pursuant to Rule 115(1) EPC, mailed May 24, 2018, for European Patent Application No. 15187477.3, filed Sep. 9, 2005, 9 pages.

Written Opinion Of International Search Authority, Application No. PCT/US2009/069385, dated Feb. 24, 2009, filed Dec. 23, 2009, 5 pages.

Written Opinion Of International Search Authority, Application No. PCT/GB2005/002289, filed Jul. 9, 2005, 7 pages.

\* cited by examiner

TARGET POPULATIONS OF OLIGODENDROCYTE PRECURSOR CELLS AND METHODS OF MAKING AND USING SAME

CROSS REFERENCE TO RELATED APPLICATION

This patent application is a divisional application of U.S. patent application Ser. No. 12/646,228, filed on Dec. 23, 2009, which claims priority to U.S. Provisional Application No. 61/140,410, filed on Dec. 23, 2008, the disclosure of each which is hereby incorporated herein by reference in its entirety.

FIELD OF THE INVENTION

This invention relates to isolation, characterization, proliferation, differentiation and transplantation of a population of oligodendrocyte precursor cells.

BACKGROUND

During development of the central nervous system ("CNS"), multipotent neural precursor cells, also known as neural stem cells, proliferate and give rise to transiently dividing progenitor cells that eventually differentiate into the cell types that compose the adult brain. Stem cells (from other tissues) have classically been defined as having the ability to self-renew (i.e., form more stem cells), to proliferate, and to differentiate into different phenotypic lineages. In the case of neural stem cells, this includes neurons, astrocytes and oligodendrocytes. Neural stem cells have been isolated from several mammalian species, including mice, rats, pigs and humans. See, e.g., WO 93/01275, WO 94/09119, WO 94/10292, WO 94/16718 and Cattaneo et al., Mol. Brain Res., 42, pp. 161-66 (1996), the disclosures of which are herein incorporated by reference in their entireties. The main function of oligodendrocytes is the myelination of axons in the central nervous system of higher vertebrates. Oligodendrocyte precursor cells (OPCs) precede oligodendrocytes.

SUMMARY

The invention provides for enriched target populations of oligodendrocyte precursor cells (OPCs) that can further differentiate into oligodendrocytes. According to some embodiments, populations of OPCs are provided that are substantially enriched for cells expressing the PDGFRα antigen.

According to some embodiments, the target OPCs are PDGFRα$^+$ and additionally CD105$^-$. According to some embodiments, the target populations of cells are enriched for OPCs that are immunopositive for PDGFRα (PDGFRα$^+$) and immunonegative for CD105 (CD105$^-$. According to some embodiments, the target populations of cells are enriched for OPCs that are immunopositive for PDGFRα (PDGFRα$^+$), immunopositive for CD133 (CD133$^+$), and immunonegative for CD105 (CD105$^-$).

According to some embodiments, the target OPCs are PDGFRα$^+$ and additionally A2B5$^{lo}$, A2B5$^-$, or mixture thereof (A2B5$^{lo/-}$). According to some embodiments, the target populations of cells are enriched for OPCs that are immunopositive for PDGFRα (PDGFRα$^+$), immunopositive for CD133 (CD133$^+$), and immunonegative for A2B5 (A2B5$^-$). According to some embodiments, the target population of OPCs are PDGFRα$^+$, A2B5$^{lo/-}$. According to some other embodiments, the target population of OPCs are PDGFRα, CD133$^+$, A2B5$^-$. According to some other embodiments, the target population of OPCs are PDGFRα$^+$, CD133$^+$, A2B5$^{lo/-}$. According to some other embodiments, the target population of OPCs are PDGFRα$^+$, CD133$^+$, A2B5$^-$, PSA-NCAM$^-$. According to some other embodiments, the target population of OPCs are PDGFRα$^+$, CD133$^+$, A2B5$^{lo/-}$, PSA-NCAM$^-$. According to some other embodiments, the target population of OPCs are PDGFRα$^+$, CD133$^+$, A2B5$^-$, PSA-NCAM$^{lo/-}$. According to some other embodiments, the target population of OPCs are PDGFRα$^+$, CD133$^+$, A2B5$^{lo/-}$, PSA-NCAM$^{lo/-}$.

According to some embodiments, the target OPCs are PDGFRα$^+$, CD105$^-$ and additionally A2B5$^{lo}$, A2B5$^-$, or mixture thereof (A2B5$^{lo/-}$). According to some embodiments, the target populations of cells are enriched for OPCs that are immunopositive for PDGFRα (PDGFRα$^+$), immunopositive for CD133 (CD133$^+$), immunonegative for A2B5 (A2B5$^-$), and immunonegative for CD105 (CD105$^-$). According to some embodiments, the target population of OPCs are PDGFRα$^+$, CD105$^-$, A2B5$^{lo/-}$. According to some other embodiments, the target population of OPCs are PDGFRα$^+$, CD133$^+$, CD105$^-$, A2B5$^-$. According to some other embodiments, the target population of OPCs are PDGFRα$^+$, CD133$^+$, CD105$^-$, A2B5$^{lo/-}$ According to some other embodiments, the target population of OPCs are PDGFRα$^+$, CD133$^+$, CD105$^-$, A2B5$^-$, PSA-NCAM. According to some other embodiments, the target population of OPCs are PDGFRα$^+$, CD133$^+$, CD105$^-$, A2B5$^{lo/-}$, PSA-NCAM$^-$. According to some other embodiments, the target population of OPCs are PDGFRα$^+$, CD133$^+$, CD105$^-$, A2B5$^-$, PSA-NCAM$^{lo/-}$. According to some other embodiments, the target population of OPCs are PDGFRα$^+$, CD133$^+$, CD105$^-$, A2B5$^{lo/-}$, PSA-NCAM$^{lo/-}$.

According to some embodiments, methods of identifying, isolating, or enriching target populations of oligodendrocyte precursor cells, are achieved by contacting a population of cells containing at least one OPC with a reagent that binds to the surface marker antigen expressed on the cell surface of an OPC. According to preferred embodiments, enriched populations of target oligodendrocyte precursor cells are achieved by contacting a population of cells containing at least one OPC with a reagent that binds to PDGFRα. Preferably, the reagent is an antibody that binds to PDGFRα. Use of traditional techniques for cell sorting, such as by immunoselection (e.g., FACS), permits identification, isolation, and/or enrichment for cells in which contact between the reagent and the PDGFRα antigen has been detected.

According to some embodiments, the invention provides methods for producing populations enriched for target oligodendrocyte precursor cells by contacting neural or neural derived cells with a monoclonal antibody that binds to a negative selection marker that is not found on the target oligodendrocyte precursor cells; selecting the cells that bind to this monoclonal antibody; and removing the bound cells. The remaining cells in the population are enriched for oligodendrocyte precursor cells. Those skilled in the art will recognize that a negative selection marker is a marker (i.e., an antigen) that is present only on non-OPC cells. In various embodiments, the monoclonal antibody may be fluorochrome conjugated or may be conjugated to magnetic particles, and the selection may be by fluorescence activated cell sorting, high gradient magnetic selection, by attachment to and disattachment from the solid phase, or any other commonly used selection technique. In preferred embodiments, the population containing neural or neural-derived cells is obtained from a suspension culture, an adherent culture, or from fresh neural tissue. These methods may also involve the step of further enriching the population for oligodendrocyte precursor cells by contacting the remaining cells with a second antibody or series of antibodies. For example, target populations of OPCs may be enriched by contacting the culture of neural or neural derived cells with an antibody that specifically binds to CD133 followed by contacting the remaining cells with an antibody that specifically binds PDGFRα to produce populations enriched for oligodendrocyte precursor cells that are immunopositive for both CD133 and PDGFRα. In addition the culture of neural or neural derived cells may be contacted with an antibody that specifically binds PDGFRα to produce populations enriched for OPCs that are immunopositive for PDGFRα.

According to some embodiments, the invention provides methods for isolating a oligodendrocyte precursor cell (OPC), by selecting from a population of neural or neural-derived cells for cells that are immunopositive for CD133 ($CD133^+$ cells); eliminating the non-immunoreactive ($CD133^-$) cells from the population; and selecting from the remaining population for at least one cell that is immunopositive for PDGFRα ($PDGFRα^+$), e.g., binds to monoclonal antibody PDGFRα. In other embodiments, the invention provides methods for producing a population enriched for oligodendrocyte precursor cells by contacting neural or neural derived cells containing at least one multipotent neural stem cell with an antibody that specifically binds to PDGFRα and selecting those cells that are $PDGFRα^{hi}$, wherein the selected cells are enriched for oligodendrocyte precursor cells as compared with the neural or neural derived cells. Those skilled in the art will recognize that the neural or neural derived cells can be obtained from a neurosphere culture (cell clusters or cell aggregates) or from an adherent culture. In some embodiments, this method also involves the step of eliminating those cells that are $PDGFRα^{lo/med}$ from the population.

According to some embodiments, the invention provides methods for isolating a oligodendrocyte precursor cell (OPC), by selecting from a population of neural or neural-derived cells for cells that are immunonegative for CD105 ($CD105^-$ cells); eliminating the immunoreactive ($CD105^+$) cells from the population; and selecting from the remaining population for at least one cell that is immunopositive for PDGFRα ($PDGFRα^+$), e.g., binds to monoclonal antibody PDGFRα. According to some embodiments, the invention provides methods for isolating a oligodendrocyte precursor cell (OPC), by selecting from a population of neural or neural-derived cells for cells that are immunopositive for PDGFRα ($PDGFRα^+$), e.g., binds to monoclonal antibody PDGFRα; eliminating the non-immunoreactive ($PDGFRα^-$) cells from the population; and selecting from the remaining population for at least one cell that is immunonegative for CD105 ($CD105^-$).

In other embodiments, the invention provides methods for producing a population enriched for oligodendrocyte precursor cells by contacting neural or neural derived cells containing at least one multipotent neural stem cell with an antibody that specifically binds to PDGFRα and selecting those cells that are $PDGFRα^{hi}$, wherein the selected cells are enriched for oligodendrocyte precursor cells as compared with the neural or neural derived cells. Those skilled in the art will recognize that the neural or neural derived cells can be obtained from a neurosphere culture or from an adherent culture. In some embodiments, this method also involves the step of eliminating those cells that are $PDGFRα^{lo/med}$ from the population.

According to some embodiments, the invention provides methods for producing a population enriched for oligodendrocyte precursor cells by eliminating cells that are positive for markers of differentiated cells or fibroblasts cells from a population of neural or neural-derived cells (e.g., CD 105). This may be accomplished by contacting the population with a monoclonal antibody directed to such markers of differentiated cells and removing those cells that bind to this monoclonal antibody. This resulting population of cells may be further enriched using any of the methods described herein. By way of non-limiting example, the method may involve the step of further enriching the population for oligodendrocyte precursor cells by contacting the remaining cells with an antibody that specifically binds to PDGFRα. In various other preferred embodiments, the fraction may optionally be enriched by selecting from the remaining cells for cells are $PDGFRα^+$, $CD105^-$, $CD133^+$, $A2B5^{lo/-}$, $PSA-NCAM^{lo/-}$ and mixtures and combinations thereof.

According to additional embodiments, the invention provides methods for proliferating enriched populations of oligodendrocyte precursor cells by introducing at least one selected cell to a serum-free culture medium containing one or more growth factors selected from the group consisting of LIF, EGF, bFGF, PDGF-AA, PDGF-AB, PDGF-BB, Sonic hedgehog (Shh), IGF1, CTNF, Noggin, and NT3 and combinations thereof; and proliferating at least one selected cell in the culture medium. Preferably, the method for proliferating enriched populations of oligodendrocyte precursor cells comprises introducing at least one selected cell to a serum-free culture medium containing one or more growth factors selected from the group consisting of PDGF-AA, NT3, bFGF, IGF1 and combinations thereof; and proliferating at least one selected cell in the culture medium.

Also provided are methods of proliferating and differentiating target OPCs. According to some embodiments, the induction of proliferation (and differentiation) of the OPCs can be done either by culturing the cells in suspension or on a substrate onto which they can adhere. Alternatively, proliferation and differentiation of OPCs can be induced, under appropriate conditions, in the host in the following combinations: (1) proliferation and differentiation in vitro, then transplantation, (2) proliferation in vitro, transplantation, then further proliferation and differentiation in vivo, (3) proliferation in vitro, transplantation and differentiation in vivo, and (4) proliferation and differentiation in vivo. Proliferation and differentiation in vivo or in situ can involve a non-surgical approach that coaxes OPCs to proliferate in vivo with pharmaceutical manipulation.

According to some embodiments, methods are provided for treating or ameliorating a demyelinating or dysmyelinating disease or disorder in a mammal, comprising administering to the mammal a target OPC or a population of target OPCs.

The mammal preferably harbors a demyelinating or dysmyelinating disease, including, but not limited to, multiple sclerosis, acute disseminated encephalomyelitis, diffuse cerebral sclerosis, necrotizing hemorrhagic encephalitis, radiation induced myelination disorders, transverse myelitits, Pelizaeus-Merzbacher disease (PMD), Cerebral palsy (CP), and leukodystrophies. The disease is preferably multiple sclerosis, Pelizaeus-Merzbacher disease, or Cerebral palsy. The mammal may additionally receive at least one biological agent that is capable of increasing the number of OPCs and/or at least one factor that is known to stimulate oligodendrocyte differentiation, growth, proliferation, or survival. The OPCs, oligodendrocyte promoting factor(s), biological agent(s), and/or other factor(s) may be administered in any manner that results in contact of the factor and or agent with target OPCs in the mammal, such as systemically (e.g., subcutaneously) or in situ. Preferably, the OPCs, oligodendrocyte promoting factor(s), biological agent(s), and/or other factor(s) may be administered into the brain, more preferably into the lateral ventricle of the brain or into the brain parenchyma.

DETAILED DESCRIPTION OF THE PREFERRED EMBODIMENTS

Figure 1:
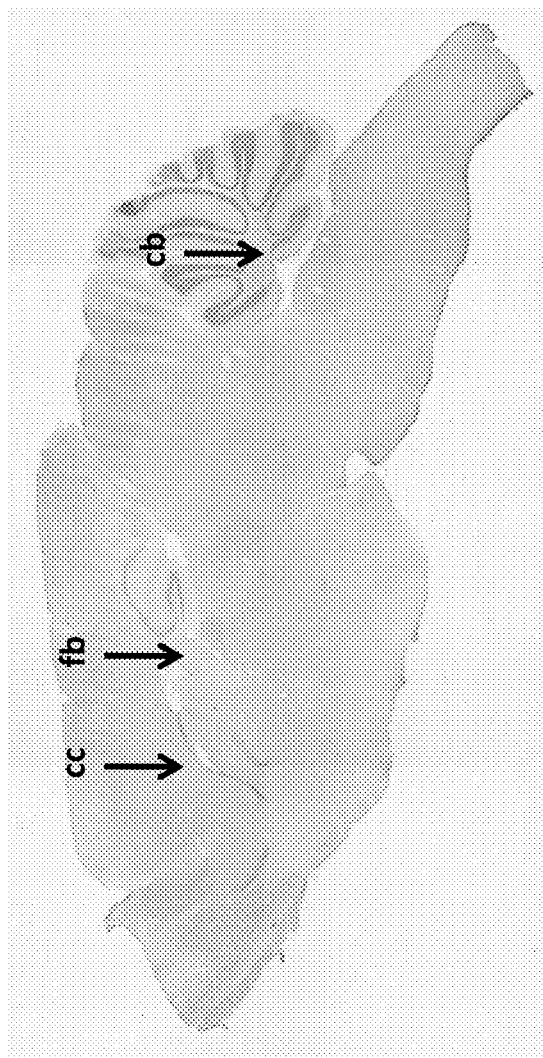
FIG. 1. Sagital section of shiverer/scid mouse counter stained with methyl green to highlight cell nuclei. Arrows indicate the 3 areas of the brain injected with human OPCs. Abbreviations: cc, corpus callosum; fb, fimbria; cb, cerebellum.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

The section headings are used herein for organizational purposes only, and are not to be construed as in any way limiting the subject matter described.

Definitions

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a cell" includes a plurality of such cells, and a reference to "an antibody" is a reference to one or more antibodies, and so forth.

As used herein, the term "target cell population" denotes those cells which are desirably being purified or enriched. Preferably, the target cell population are oligodendrocyte precursor cells that display the distinctive pattern of cell markers as described herein.

"Oligodendrocytes" (OLs) or oligodendroglia are best known as the myelin-forming cells of the central nervous system (CNS). The term "oligodendrocyte precursor cell" or "OPC" refers to the immature form of oligodendrocytes that are capable of differentiating into myelin forming cells of the CNS under certain conditions. This term includes oligodendrocyte precursor cells isolated from primary tissue and cells cultured in vitro into OPCs, as well as the progeny of such oligodendrocyte precursor cells, and thus includes both OPCs and daughter OPCs.

The term "neural stem cells" is the more general term used for undifferentiated, multipotent, self-renewing, neural cells. A neural stem cell is a clonogenic multipotent stem cell which is able to divide and, under appropriate conditions, has self-renewal capability and can include in its progeny daughter cells which can terminally differentiate into neurons, astrocytes, and oligodendrocytes. Hence, the neural stem cell is "multipotent" because stem cell progeny have multiple differentiation pathways. A neural stem cell is capable of self maintenance, meaning that with each cell division, one daughter cell will also be a stem cell.

The non-stem cell progeny of a neural stem cell are typically referred to as "progenitor" or "precursor" cells, which are capable of giving rise to various cell types within one or more lineages. The term "neural progenitor cell" or "neural precursor cell" refers to an undifferentiated cell derived from a neural stem cell and is not itself a stem cell. Some progenitor cells can produce progeny that are capable of differentiating into more than one cell type. For example, an O-2A cell is a glial progenitor cell that gives rise to oligodendrocytes and type II astrocytes, and, thus, could be termed a "bipotential" progenitor cell. A distinguishing feature of a progenitor cell is that, unlike a stem cell, it does not exhibit self maintenance. Moreover, progenitor cells are typically thought to be committed to a particular path of differentiation and will, under appropriate conditions, eventually differentiate into glia or neurons.

The terms "neural cells" or "neural derived cells" refers broadly to cells associated with the central nervous system (CNS) of an organism, for example, neurons, glial cells, and precursor cells. As used herein, neural cells may be cells that are isolated or derived from neural tissue, as well as any cell, regardless of origin, having at least an indication of neuronal or glial phenotype, such as staining for one or more neuronal or glial markers or which will differentiate into cells exhibiting neuronal or glial markers. Thus, the term may be used as a general teem to refer to, for example, primary cells isolated and cultured in vitro; cultured immortalized cells derived from a neural tissue, neural tissue cells; and/or cells cultured to express a neural phenotype. The term is meant to be all-encompassing with respect to cells exhibiting a neural cell phenotype and/or isolated from neural tissue. Thus, the term neural cells also includes cells which are neural precursor cells as well as differentiated neural cells. As used herein, the term "neuronal cells" refers to neurons.

The term "positive selection" refers to a process in which the target cell population is purified or enriched by removing the target cell population from a mixture of cell populations by directly binding the target cell population to reagents having affinity therefore.

In contrast, the term "negative selection" refers to a process in which the target cell population is purified or enriched by removing nontarget cell populations from the mixture of cells by binding the nontarget cell populations to reagents having affinity therefore. For example, CD45 is the T200/leucocyte common antigen. Human central nervous system stem cells (CNS-SC), and preferably those that can initiate neurospheres, and cultures containing them, are additionally characterized as lacking certain cell surface markers such as CD45. Thus, reagents that recognize CD45 may be useful in a negative selection process to remove nontarget cells.

A "primary neurosphere" is a neurosphere generated by culturing brain tissue. Typically, the brain tissue is dissected and mechanically dissociated before being cultured in appropriate media and allowed to form neurospheres. Exemplary methods are described in, for instance, U.S. Pat. No. 5,750,376, the disclosure of which is incorporated herein by reference in its entirety.

A "secondary neurosphere" is a neurosphere generated by dissociating (passaging) a primary neurosphere and culturing the dissociated cells under conditions which result in the formation of neurospheres from single cells.

A "mammal" is any member in the mammalian family. A mammal is preferably a primate, rodent, feline, canine, domestic livestock (such as cattle, sheep, goats, horses, and pigs), and most preferably a human.

A "demyelinating disease" or a "dysmyelinating disorder" is a disease, disorder, or medical condition that is caused by or associated with inadequate amounts myelin. Demyelination is the process of myelin removal i.e., loss of myelin that existed before. Dysmyelination occurs where no or inadequate amounts of myelin forms, e.g., due to dysfunctional OPCs or oligodendrocytes (OLs). The end result of demyelination and dysmyelination is hypomyelination. Examples of these diseases, disorders, or conditions include, for example, multiple sclerosis (including the relapsing and chronic progressive forms of multiple sclerosis, acute multiple sclerosis, neuromyelitis optica (Devic's disease)), diffuse cerebral sclerosis (including Shilder's encephalitis periaxialis diffusa and Balo's concentric sclerosis). Demyelinating diseases or dysmyelinating disorders also include a variety of diseases wherein demyelination is caused by viral infections, vaccines, spinal cord injury, and genetic disorders. Examples of these demyelinating diseases or dysmyelinating disorders include acute disseminated encephalomyelitis (occurring after measles, chicken pox, rubella, influenza or mumps; or after rabies or small pox vaccination), necrotizing hemorrhagic encephalitis (including hemorrhagic leukoencephalitis), and leukodystrophies (including Krabbels globboid leukodystrophy, metachromatic leukodystrophy, adrenoleukodystrophy, adrenomyeloneuropathy, adrenomyeloneuropathy, radiation induced myelination disorders, transverse myelitits, Pelizaeus-Merzbacher disease (PMD), Canavan's disease and Alexander's disease). The demyelinating disease or dysmyelinating disorder is preferably multiple sclerosis, cerebral palsy, diffuse cerebral sclerosis, or Pelizaeus-Merzbacher disease (PMD), and, most preferably, Pelizaeus-Merzbacher disease.

"Treating" or "ameliorating" means the reduction or complete removal of the symptoms of a disease or medical condition.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

The term "ventricle" refers to any cavity or passageway within the CNS through which cerebral spinal fluid flows. Thus, the term not only encompasses the lateral, third, and fourth ventricles, but also encompasses the central canal, cerebral aqueduct, and other CNS cavities.

Cell Markers

This invention provides for the identification, isolation, enrichment, and culture of oligodendrocyte precursor cells. The target cell population of OPCs can be characterized by their expression of cell surface markers. While it is commonplace in the art to refer to cells as "positive" or "negative" for a particular marker, actual expression levels are a quantitative trait. The number of molecules on the cell surface can vary by several logs, yet still be characterized as "positive". It is also understood by those of skill in the art that a cell which is negative for staining, i.e., the level of binding of a marker specific reagent is not detectably different from a control, e.g. an isotype matched control; may express minor amounts of the marker. Characterization of the level of staining permits subtle distinctions between cell populations.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest cells in a population are designated as 4 logs (i.e., 10,000 times) mom intense than the cells having the lowest level of staining. When displayed in this manner, it is clear that the cells falling in the highest log of staining intensity are bright, while those in the lowest intensity am negative. The "low" staining cells, which fall in the 2-3 log (i.e., 100-1000 fold) of staining intensity, may have properties that are unique from the negative and positive cells. An alternative control may utilize a substrate having a defined density of marker on its surface, for example a fabricated bead or cell line, which provides the positive control for intensity. The "low" designation indicates that the level of staining is above the brightness of an isotype matched control, but is not as intense as the most brightly staining cells normally found in the population.

For the purpose of defining staining intensity of a particular antibody, an isotype matched control will define the signal intensity of "non-specific" or "negative" staining. Whereas any staining which results in signal intensity above that of the control is considered to be "positive" staining The boundary demarcating negative and positive staining is conventionally set such that the frequency of events to the left of, or below, the boundary is >0.99 and <1.0. Positive staining intensity can then be further subdivided and categorized as low, medium, or high by defining an arbitrary scale from the control boundary to the highest recorded signal intensity and defining two additional lines of demarcation at the 33$^{rd}$ and 66$^{th}$ percentiles, respectively. Signals measured in the lower-third, middle-third, and upper-third of these defined groups can then be designated as low, medium, and high staining intensity, respectively.

Cell Sorting

The use of cell surface antigens to isolate, select, or enrich for OPC cells provides a means for the positive and negative immunoselection of target OPC populations, as well as for the phenotypic analysis of target OPC cell populations using flow cytometry. For the preparation of substantially pure target OPC populations, a subset of OPCs is separated from other cells on the basis of PDGFRα binding. OPCs may be further separated by binding to other surface markers known in the art. Cells selected for expression of PDGFRα antigen, for example, may be further purified by the positive and negative immunoselection of other target OPC markers as disclosed herein.

Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide [PI], LDS). Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. PDGFRα$^+$, CD105$^-$, CD133$^+$, CD24$^-$, etc. Fluorochromes which find use in a multi-color analysis include, for example, phycobiliproteins, e.g. phycoerythrin and allophycocyanins; fluorescein and Texas red. A negative designation indicates that the level of staining is at or below the brightness of an isotype matched negative control. A "dim", "lo", or "low" designation indicates that the level of staining may be near the level of a negative stain, but may also be brighter than an isotype matched control.

For example, the PDGFRα antibody is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sulfhydryl groups and heterofunctional cross-linking reagents. A large number of heterofunctional compounds are available for linking to entities. A preferred linking group is 3-(2-pyridyidithio) propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, the antibody is indirectly coupled to the magnetic particles. The antibody may be directly conjugated to a hapten, and hapten-specific, second stage antibodies are conjugated to the particles. Suitable haptens include, for examples digoxin, digoxigenin, F1TC, dinitrophenyl, nitrophenyl, avidin, biotin, etc. Methods for conjugation of the hapten to a protein, i.e. are known in the art, and kits for such conjugations are commercially available.

Target OPC populations are selected by bringing neural or neural-derived cells into contact with the antibody or reagent that binds the surface marker. For example, antibody is added to a cell sample. The amount of antibody or other reagent necessary to bind a particular cell subset is empirically determined by performing a test separation and analysis. For example, the cells and antibody/reagent are incubated for a period of time sufficient for complexes to form, preferably at least about 5 min, more preferably at least about 10 min, and usually not more than one hr, more usually not more than about 30 min. The cells may additionally be incubated with antibodies or binding molecules specific for cell surface markers known to be present or absent on OPCs.

The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520, the disclosures of which are herein incorporated by reference in their entireties.

The purified cell population may be collected in any appropriate medium. Various media are commercially available and may be used, including Dulbecco's Modified Eagle Medium (DMEM), Hank's Basic Salt Solution (HBSS), Dulbecco's phosphate buffered saline (DPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), etc.

Populations highly enriched for target OPCs are achieved in this manner. The desired cells will be 30% or more of the cell composition, preferably 50% or more (e.g., 60% or more, 70% or more, 75% or more, 80% or more, 85% or more, 90% or more, 95% or more) of the cell population, more preferably 90% or more (e.g., 92% or more, 94% or more, 96% or more, or 98% or more) of the cell population, and most preferably 95% or more (e.g., 97%, 99%) (substantially pure) of the cell population. The degree of enrichment obtained, and actually used, depends on a number of factors, including, but not limited to, the method of selection, the method of growth, and/or the dose of the cells that are placed in culture.

Isolation, Enrichment, and Selection of Cells

The invention provides for the isolation and identification of OPCs. The methods of this invention may be used to isolate PDGFRα$^+$ cells from PDGFRα$^-$ cells using an PDGFRα antibody or other reagent that specifically binds to PDGFRα by combining a population of neural or neural-derived cells which contains a fraction of OPCs with the antibody or reagent, and then selecting for PDGFRα$^+$ cells, to produce a selected population enriched in PDGFRα$^+$ OPCs as compared with the population of neural or neural-derived cells before selection.

The population of cells from which OPCs are isolated is preferably a neural tissue, a population of cells dissociated from neural tissue, a population of cells that can give rise to neural cells or neural tissue, or a population of cells in cell culture, e.g., cells in a neurosphere culture or an adherent neural stem cell culture. Identification of oligodendrocyte precursor cell (OPC) involves contacting a population of cells or neural cells (or tissue which contains neural or neural-derived cells) with a reagent that binds to cell surface markers expressed by the target population of OPCs. For example, the method may comprise contacting a population of neural or neural-derived cells with a reagent that binds to PDGFRα (e.g., a monoclonal antibody) and detecting the contact between the reagent that binds to PDGFRα and PDGFRα on the surface of cells. Target OPCs are included in the population of cells that reagent binds to the reagent. The identity of those cells can be confirmed by any assays known on the art to demonstrate that the cells are, in fact, OPCs, i.e., capable of proliferation and capable of differentiating into mature oligodendrocytes.

The OPCs according to some embodiments may be further characterized as being immunonegative for CD105 (CD105−). Accordingly, the method of identifying, isolating, or enriching populations of oligodendrocyte precursor cells may additionally compromise selecting from a population of neural or neural-derived cells for cells that are immunonegative for CD105 (CD105− cells) and eliminating the CD105+ cells from the population. Selection of CD105− cells may then be followed by selecting from the remaining population for at least one cell that is immunopositive for PDGFRα (PDGFRα+). In the alternative, the invention provides methods for isolating a oligodendrocyte precursor cell (OPC), by selecting from a population of neural or neural-derived cells for cells that are immunopositive for PDGFRα (PDGFRα+), e.g., binds to monoclonal antibody PDGFRα; eliminating the non-immunoreactive (PDGFRα−) cells from the population; and selecting from the remaining population for cells that are immunonegative for CD105 (CD105−), i.e., eliminating CD105+ cells from the population.

The OPCs according to some embodiments may be further characterized as being immunopositive for CD133 (CD133+). Accordingly, the method of identifying, isolating, or enriching populations of oligodendrocyte precursor cells may additionally comprise selecting from a population of neural or neural-derived cells for cells that are immunopositive for CD133 (CD133+ cells) and eliminating the CD133− cells from the population. Selection of CD133+ cells may then be followed by selecting from the remaining population for at least one cell that is immunopositive for PDGFRα (PDGFRα+).

Accordingly, the invention further provides for the enrichment of target OPCs from neural tissue or neural stem cell cultures (e.g., suspension cultures or adherent cultures). The methods and composition of the invention are thus useful for the enrichment of target OPC from neural tissue in which stem cells and progenitor cells occur at low frequency, or may have been depleted, such as late embryo, juvenile, and adult tissue. Thus, one of skill in the art can combine a population of neural or neural-derived cells containing a fraction of target OPCs with a reagent that specifically binds to, for example, PDGFRα, and then select for the PDGFRα+ cells. In this way, the selected PDGFRα+ cells are enriched in the fraction of OPC as compared with the population of neural or neural-derived cells. According to preferred embodiments, the target OPCs may be characterized based on a medium to high expression of PDGFRα (e.g., PDGFRα$^{med}$ or PDGFRα$^{high}$). For example, target OPCs are included in the PDGFRα+ cells sorted from suspended neurospheres based on medium to high expression (e.g., PDGFRα$^{med}$ or PDGFRα$^{high}$). Target OPCs may be further identified by their expression of the markers CD105, CD133, A2B5, PSA-NCAM, O4, and/or NG2 in accordance with the present invention.

Any method for selecting a population of cells on the basis of cell marker expression known in the art may be used to select for the OPCs of the present invention. For example, the identification of PDGFRα+ and/or CD133+ target cell populations may involve contacting a population of neural cells (or tissue which contains neural or neural derived cells) with a reagent that binds to PDGFRα and/or CD133, and detecting the contact between the reagent that binds to PDGFRα and/or CD133 and PDGFRα and/or CD133 on the surface of cells. Target OPCs are included in the population of those cells to which the reagent binds. The identity of those cells can be confirmed by assays to demonstrate that the cells are, in fact, OPCs, i.e., they are capable of differentiating into mature oligodendrocytes. Use of traditional techniques for cell sorting, such as by immunoselection (e.g., fluorescence activated cell separation (FACS)), permits identification, isolation, and/or enrichment for cells in which contact between the reagent and the PDGFRα antigen has been detected.

One of skill in the art can introduce an isolated target OPC(s) to a culture medium; proliferate the isolated target OPC(s) in culture; culture the progeny of the isolated target OPC(s) under conditions in which the isolated target OPC(s) differentiates into oligodendrocytes, and detect the presence of oligodendrocytes, The presence of oligodendrocytes characterizes the isolated target OPC(s) as an OPC.

Any cell markers known in the art may also be used for the positive and negative selection of OPCs. For example, monoclonal antibodies (mAb) against human CD45 may be used to exclude blood cell contamination in fetal tissue. In some cases, mAb against human CD34 may be used to exclude endothelial cells and endothelial-neural progenitor complexes. In some cases, antibodies against human CD24 may be used to exclude those cells that are not likely to initiate neurospheres. Any of these antibodies may be used alone, in combination, or sequentially in the methods for enriching the target cell populations disclosed herein.

Using the techniques and methods disclosed herein, one of skill in the art can derive the population of target OPCs by immunoselection using the appropriate antibody or series of preferred antibodies. According to some embodiments, the population of target cells contains at least 30% PDGFRα+ OPCs, preferably at least 50-70% PDGFRα+ OPCs, and more preferably greater than 90% PDGFRα+ OPCs (e.g., 92% or more, 94% or more, 96% or more, or 98% or more). Most preferable would be a substantially pure population of PDGFRα+ OPCs, comprising at least 95% PDGFRα+ OPCs (e.g., 97% or 99%).

According to some embodiments, the population of target cells contains at least 30% PDGFRα+, CD105− OPCs, preferably at least 50-70% PDGFRα+, CD105− OPCs, and more preferably greater than 90% PDGFRα+, CD105− OPCs (e.g., 92% or more, 94% or more, 96% or more, or 98% or more). Most preferable would be a substantially pure population of PDGFRα+, CD105− OPCs, comprising at least 95% PDGFRα+, CD105− OPCs (e.g., 97% or 99%).

According to some embodiments, the population of target cells contains at least 30% PDGFRα+, A2B5− OPCs, preferably at least 50-70% PDGFRα+, A2B5− OPCs, and more preferably greater than 90% PDGFRα+, A2B5− OPCs (e.g., 92% or more, 94% or more, 96% or more, or 98% or more). Most preferable would be a substantially pure population of PIDGFRa+, A2B5− OPCs, comprising at least 95% PDGFRα+, A2B5− OPCs (e.g., 97% or 99%). According to some embodiments, the population of target cells is additionally immunonegative for CD105 (CD105−).

According to some embodiments, the population of target cells contains at least 30% PDGFRα$^+$, A2B5$^{lo/-}$ OPCs, preferably at least 50-70% PDGFRα$^+$, A2B5$^{lo/-}$ OPCs, and more preferably greater than 90% PDGFRα$^+$, A2B5$^{lo/-}$ OPCs (e.g., 92% or more, 94% or more, 96% or more, or 98% or more). Most preferable would be a substantially pure population of PDGFRα$^+$, A2B5$^{lo/-}$ OPCs, comprising at least 95% PDGFRα$^+$, A2B5$^{lo/-}$ OPCs (e.g., 97% or 99%). According to some embodiments, the population of target cells is additionally immunonegative for CD105 (CD105$^-$).

According to some embodiments, the population of target cells contains at least 30% PDGFRα$^{med/high}$, A2B5$^-$ OPCs, preferably at least 50-70% PDGFRce$^{med/high}$ A2B5$^-$ OPCs, and more preferably greater than 90% PDGFRα$^{med/high}$, A2B5$^-$ OPCs (e.g., 92% or more, 94% or more, 96% or more, or 98% or more). Most preferable would be a substantially pure population of PDGFRα$^{med/high}$, A2B5$^-$ OPCs, comprising at least 95% PDGFRα$^{med/high}$, A2B5$^-$ OPCs (e.g., 97% or 99%). According to some embodiments, the population of target cells is additionally immunonegative for CD105 (CD105$^-$).

According to some embodiments, the population of target cells contains at least 30% PDGFRα$^{med/high}$, A2B5$^{lo/-}$ OPCs, preferably at least 50-70% PDGFRα$^{med/high}$, A2B5$^{lo/-}$ OPCs, and more preferably greater than 90% PDGFRα$^{med/high}$, A2B5$^{lo/-}$ OPCs (e.g., 92% or more, 94% or more, 96% or more, or 98% or more). Most preferable would be a substantially pure population of PDGFRα$^{med/high}$, A2B5$^{lo/-}$ OPCs, comprising at least 95% PDGFRα$^{med/high}$, A2B5$^{lo/-}$ OPCs (e.g., 97% or 99%). According to some embodiments, the population of target cells is additionally immunonegative for CD105 (CD105$^-$).

According to some embodiments, the population of target cells contains at least 30% PDGFRα$^+$, PSA-NCAM$^-$ OPCs, preferably at least 50-70% PDGFRα$^+$, PSA-NCAM$^-$ OPCs, and more preferably greater than 90% PDGFRα$^+$, PSA-NCAM OPCs (e.g., 92% or more, 94% or more, 96% or more, or 98% or more). Most preferable would be a substantially pure population of PDGFRα$^+$, PSA-NCAM$^-$ OPCs, comprising at least 95% PDGFRα$^+$, PSA-NCAM$^-$ OPCs (e.g., 97% or 99%). According to some embodiments, the population of target cells is additionally immunonegative for CD105 (CD105$^-$).

According to some embodiments, the population of target cells contains at least 30% PDGFRα$^+$, PSA-NCAM$^{lo/-}$ OPCs, preferably at least 50-70% PDGFRα$^+$, PSA-NCAM$^{lo/-}$ OPCs, and more preferably greater than 90% PDGFRα$^+$, PSA-NCAM$^{lo/-}$ OPCs (e.g., 92% or more, 94% or more, 96% or more, or 98% or more). Most preferable would be a substantially pure population of PDGFRα$^+$, PSA-NCAM$^{lo/-}$ OPCs, comprising at least 95% PDGFRα$^+$, PSA-NCAM$^{lo/-}$ OPCs (e.g., 97% or 99%). According to some embodiments, the population of target cells is additionally immunonegative for CD105 (CD105$^-$).

According to some embodiments, the population of target cells contains at least 30% PDGFRα$^{med/high}$, PSA-NCAM$^-$ OPCs, preferably at least 50-70% PDGFRα$^{med/high}$, PSA-NCAM$^-$ OPCs, and more preferably greater than 90% PDGFRα$^{med/high}$, PSA-NCAM$^-$ OPCs (e.g., 92% or more, 94% or more, 96% or more, or 98% or more). Most preferable would be a substantially pure population of PDGFRα$^{med/high}$, PSA-NCAM$^-$ OPCs, comprising at least 95% PDGFRα$^{med/high}$, PSA-NCAM$^-$ OPCs (e.g., 97% or 99%). According to some embodiments, the population of target cells is additionally immunonegative for CD105 (CD105$^-$).

According to some embodiments, the population of target cells contains at least 30% PDGFRα$^{med/high}$, PSA-NCAM$^{lo/-}$ OPCs, preferably at least 50-70% PDGFRα$^{med/high}$, PSA-NCAM$^{lo/-}$ OPCs, and more preferably greater than 90% PDGFRα$^{med/high}$, PSA-NCAM$^{lo/-}$ OPCs (e.g., 92% or more, 94% or more, 96% or more, or 98% or more). Most preferable would be a substantially pure population of PDGFRα$^{med/high}$, PSA-NCAM$^{lo/-}$ OPCs, comprising at least 95% PDGFRα$^{med/high}$, PSA-NCAM$^{lo/-}$ OPCs (e.g., 97% or 99%). According to some embodiments, the population of target cells is additionally immunonegative for CD105 (CD105$^-$).

According to some embodiments, the population of target cells contains at least 30% PDGFRα$^+$, CD133$^+$, A2B5$^{lo/-}$ OPCs, preferably at least 50-70% PDGFRα$^+$, CD133$^+$, A2B5$^{lo/-}$ OPCs, and more preferably greater than 90% PDGFRα$^+$, CD133$^+$, A2B5$^{lo/-}$ OPCs (e.g., 92% or more, 94% or more, 96% or more, or 98% or more). Most preferable would be a substantially pure population of PDGFRα$^+$, CD133$^+$, A2B5$^{lo/-}$ OPCs, comprising at least 95% PDGFRα$^+$, CD133$^+$, A2B5$^{lo/-}$ OPCs (e.g., 97%, 99%). According to some embodiments, the population of target cells is additionally immunonegative for CD105 (CD105$^-$).

According to some embodiments, the population of target cells contains at least 30% PDGFRα$^+$, CD133$^+$, PSA-NCAM$^{lo/-}$ OPCs, preferably at least 50-70% PDGFRα$^+$, CD133$^+$, PSA-NCAM$^{lo/-}$ OPCs, and more preferably greater than 90% PDGFRα$^+$, CD133$^+$, PSA-NCAM$^{lo/-}$ OPCs (e.g., 92% or more, 94% or more, 96% or more, or 98% or more). Most preferable would be a substantially pure population of PDGFRα$^+$, CD133$^+$, PSA-NCAM$^{lo/-}$ OPCs, comprising at least 95% PDGFRα$^+$, CD133$^+$, PSA-NCAM$^{lo/-}$ OPCs (e.g., 97%, 99%). According to some embodiments, the population of target cells is additionally immunonegative for CD105 CD105$^-$).

According to some embodiments, the population of target cells contains at least 30% PDGFRα$^+$, A2B5$^{lo/-}$, PSA-NCAM$^{lo/-}$ OPCs, preferably at least 50-70% PDGFRα$^+$, A2B5$^{lo/-}$, PSA-NCAM$^{lo/-}$ OPCs, and more preferably greater than 90% PDGFRα$^+$, A2B5$^{lo/-}$, PSA-NCAM$^{lo/-}$ OPCs (e.g., 92% or more, 94% or more, 96% or more, or 98% or more). Most preferable would be a substantially pure population of PDGFRα$^+$, A2B5$^{lo/-}$, PSA-NCAM$^{lo/-}$ OPCs, comprising at least 95% PDGFRα$^+$, A2B5$^{lo/-}$, PSA-NCAM$^{lo/-}$ OPCs (e.g., 97%, 99%). According to some embodiments, the population of target cells is additionally immunonegative for CD105 (CD105$^-$).

According to some embodiments, the population of target cells contains at least 30% PDGFRα$^{med/high}$, A2B5$^{lo/-}$, PSA-NCAM$^{lo/-}$ OPCs, preferably at least 50-70% PDGFRα$^{med/high}$ A2B5$^{lo/-}$, PSA-NCAM$^{lo/-}$ OPCs, and more preferably greater than 90% PDGFRα$^{med/high}$ A2B5$^{lo/-}$, PSA-NCAM$^{lo/-}$ OPCs (e.g., 92% or more, 94% or more, 96% or more, or 98% or more). Most preferable would be a substantially pure population of PDGFRα$^{med/high}$ A2B5$^{lo/-}$, PSA-NCAM$^{lo/-}$ OPCs, comprising at least 95% PDGFRα$^{med/high}$, A2B5$^{lo/-}$, PSA-NCAM$^{lo/-}$ OPCs (e.g., 97%, 99%). According to some embodiments, the population of target cells is additionally immunonegative for CD105 (CD105$^-$).

According to some embodiments, the population of target cells contains at least 30% PDGFRα$^+$, O4$^-$ OPCs, preferably at least 50-70% PDGFRα$^+$, O4$^-$ OPCs, and more preferably greater than 90% PDGFRα$^+$, O4$^-$ OPCs (e.g., 92% or more, 94% or more, or more, or 98% or more). Most preferable would be a substantially pure population of PDGFRα$^+$, O4$^-$ OPCs, comprising at least 95% PDGFRα$^+$, O4$^-$ OPCs (e.g., 97%, 99%). According to some embodiments, the population of target cells is additionally immunonegative for CD105 (CD105⁻). The degree of enrichment obtained, and actually used, depends on a number of factors, including the method of selection, the method of growth, and/or the dose of the cells that are placed in culture.

Cryopreservation and Handling

According to some embodiments, the OPCs of the present embodiments may be cryopreserved according to routine procedures. In some embodiments, cryopreserving involves freezing about one to ten million cells in "freeze" medium, which may comprise proliferation medium and antioxidants such as NAC (0.1 to 2 mM; e.g., 0.5 mM, 1 mM, etc.). Proliferation medium is preferably absent the growth factor mitogens. For example, suspended cells may be centrifuged and any growth medium is aspirated and replaced with freeze medium. Cells may then be slowly frozen, by, e.g., placing in a container at −80° C. or frozen in liquid nitrogen. Cells are thawed by swirling in a 37° C. bath, resuspended in fresh proliferation medium, and grown as usual.

According to some embodiments, the OPCs of the present embodiments may be cryopreserved in a ready to use format (such as a pharmaceutical grade vial or container). In some embodiments, the OPCs are thawed and cultured prior to use. In some embodiments, the OPCs are thawed and cultured in suspension prior to use. In some embodiments, the OPCs are thawed and cultured on an adherent substrate prior to use. The period for culturing after thawing may be 1 to 24 hours. In some embodiments, the period for culture after thawing may be from 1 to 2 days.

According to some embodiments, the OPCs of the present invention may be held in a suspension culture format. According to some embodiments, the OPCs of the present invention may be held in a suspension culture format after detachment from a culture plate (e.g., post trypsin treatment). For example, adherent OPCs are detached by treatment with trypsin and are transferred to a suspension culture medium. The period of time in which the OPCs are held in suspension may be referred to as the "hold" period. The hold period in suspension is advantageous for at least the following 3 reasons: 1) would allow cells to recover from a potentially damaging enzyme treatment Oar to transplantation and/or cryopreservation; 2) it would introduce more flexibility in animal surgery scheduling and 3) would make shipment of ready-to-transplant OPCs to an off-site location (laboratory or clinic) possible. According to some embodiments, the hold period may be 2, 4, 6, 8, 12, 18, or 24 hours. According to some embodiments, the hold period may be 1, 2, 3, 4, 5, 6, 7, 8, 9, or 10 days.

Tissue Source

Any suitable tissue source may be used to derive the OPCs of this invention. The adult human CNS has been shown to contain oligodendrocyte precursor cells that are capable of proliferating, and which could mature into myelinating oligodendrocytes under the appropriate conditions. Accordingly, the population of cells can be derived from late embryo, juvenile, or adult mammalian CNS tissue, or it may be derived from existing cultures of neural stem cells, as described in Weiss, U.S. Pat. No. 5,750,376, or Johe, U.S. Pat. No. 5,753,506. The OPCs may also be obtained from any tissue or cellular source that is capable of giving rise to neural tissue. In one preferred embodiment, the OPCs are human.

OPCs may be been isolated from neural or neural-derived cells of several mammalian species including, but not limited to, mice, rats, pigs, non-human primates, and humans. Neural or neural-derived cells may be obtained from embryonic, fetal, post-natal, juvenile, or adult neural tissue, which includes brain and spinal cord. For example, neural or neural-derived cells may be obtained from the cerebral cortex, cerebellum, midbrain, brainstem, spinal cord, and ventricular tissue, as well as areas of the PNS including the carotid body and the adrenal medulla. Other preferred areas include regions in the basal ganglia, preferably the striatum, which consists of the caudate and putamen, or various cell groups such as the globus pallidus, the subthalamic nucleus, the nucleus basalis, the substantia nigra pars compacta, as well as from ventricular tissue found lining CNS ventricles, including the subependyma. The subventricular zone and ventral neuroepithelium are preferred source of OPCs in the adult animal.

In addition to OPCs, a population of cells exists within the adult CNS that exhibit stem cell properties in their ability to self-renew and to produce the differentiated mature cell phenotypes of the adult CNS such as oligodendrocytes. These stem cells are found throughout the CNS, particularly in the subventricular region and the dentate gyrus of the hippocampus, and represent a source of neural or neural derived cells from which the target OPCs may be isolated. Neural stem cells have also been isolated from a variety of adult CNS ventricular regions, including the frontal lobe, conus medullaris, thoracic spinal cord, brain stem, and hypothalamus.

Growth factor-responsive stem cells can be isolated from many regions of the neuraxis and at different stages of development, of murine, rodent, mammalian, and human CNS tissue. These cells vary in their response to growth factors such as EGF, basic FGF (bFGF, FGF-2) and transforming growth factor alpha (TGFα) and can be maintained and expanded in culture in an undifferentiated state for long periods of time. (See, e.g. WO93/01275 and WO94/16788, incorporated herein by reference).

Proliferation

OPCs can be induced to proliferate either by culturing the cells in suspension or on an adherent substrate. See, e.g., U.S. Pat. Nos. 5,750,376 and 5,753,506 (both incorporated herein by reference in their entirety), and medium described therein. Both allografts and autografts are contemplated for transplantation purposes.

Typically, OPCs of the present embodiments are cultured in a medium that permits their growth and proliferation. The culture in which the isolated OPCs proliferates can be a serum-free medium containing one or more predetermined growth factors effective for inducing proliferation. The culture medium may be supplemented with a growth factor selected from platelet-derived growth factor (PDGF), epidermal growth factor (EGF), basic fibroblast growth factor (FGF-2; bFGF), NT3, IGF1 or combinations thereof. The culture medium may be further supplemented with N2 and B27. The conditions in which the OPCs differentiate to oligodendrocytes include culturing the OPC progeny on a laminin or laminin plus fibronectin-coated surface in culture medium containing fetal bovine serum (FBS) or T3 (triiodothyronine) without EGF, bFGF, PDGF, NT3, IGF1 or LIF.

According to some embodiments, the OPCs of the present embodiments may be passaged from 1 to 20 times (e.g., 1, 2, 3, 4, 5, 6, 7, 8, 9, 10, 11, 12, 13, 14, 15, 16, 17, 18, 19, and 20 times) post isolation from the primary tissue source and may be induced to proliferate by culturing the cells in suspension or on an adherent substrate. Passaging (a.k.a, subculturing or splitting) typically involves detaching cells from the surface of the primary culture vessel by trypsinization or mechanical means. The resultant cell suspension is then subdivided, or reseeded, into fresh cultures. Secondary cultures are checked for growth and fed periodically, and may be subsequently subcultured to produce tertiary cultures and so on. The time between passaging of cells varies and depends on the growth rate.

The proliferation medium can be any medium known in the art to induce proliferation of the OPCs without inducing their differentiation. Example 3 provided herein provides an exemplary medium for proliferating the OPCs of the present embodiments. Cell passage or splitting is necessary to maintain cells in exponential growth. Methods for passaging or splitting cells are well known in the art. The OPCs may be passaged using any known method known in the art.

Differentiation

When OPCs are cultured under conditions that allow differentiation, progenitor cells differentiate to oligodendrocytes. Differentiation of the cells can be induced by any method known in the art, which include the liberation of inositol triphosphate and intracellular $Ca^{2+}$, liberation of diacyl glycerol, and the activation of protein kinase C and other cellular kinases, and the like. Treatment with phorbol esters, differentiation-inducing growth factors, hormones and other chemical signals can induce differentiation. Differentiation can be induced by growth factor exhaustion, for example, by removal of mitogens, by leaving the cells in culture without media renewal, or by absence of passaging.

The induction of proliferation (and differentiation) of the OPCs can be done either by culturing the cells in suspension or on a substrate onto which they can adhere. Alternatively, proliferation and differentiation of OPCs can be induced, under appropriate conditions, in the host in the following combinations: (1) proliferation and differentiation in vitro, then transplantation, (2) proliferation in vitro, transplantation, then further proliferation and differentiation in vivo, (3) proliferation in vitro, transplantation and differentiation in vivo, and (4) proliferation and differentiation in vivo. Proliferation and differentiation in vivo or in situ can involve a non-surgical approach that coaxes OPCs to proliferate in vivo with pharmaceutical manipulation. Such methods involving the transplantation of OPCs are discussed in further detail below.

Use of Purified Stem Cell/Progenitor Cells.

The target OPC populations identified using the methods described herein are useful in a variety of ways, including for drug screening, diagnostics, transplantation, and treatment. The OPCs may be used to reconstitute a host whose cells have been lost through disease or injury. Genetic diseases associated with cells may be treated by genetic modification of autologous or allogeneic OPCs to correct a genetic defect or treat to protect against disease. Alternatively, normal allogeneic OPCs may be transplanted. Diseases other than those associated with cells may also be treated, where the disease is related to the lack of a particular secreted product such as hormone, enzyme, growth factor, or the like.

CNS disorders encompass numerous afflictions such as neurodegenerative diseases (e.g. Alzheimer's and Parkinson's), acute brain injury (e.g. stroke, ischemia, head injury, cerebral palsy) and a large number of CNS dysfunctions (e.g. depression, epilepsy, and schizophrenia), In recent years neurodegenerative disease has become an important concern due to the expanding elderly population which is at greatest risk for these disorders. These diseases, which include, for example, Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function. By providing for maturation, proliferation and differentiation into oligodendrocytes through specific different growth factors, the oligodendrocyte progenitor cells may be used as a source of oligodendrocytes.

The target OPC populations may also be used in the isolation and evaluation of factors associated with the differentiation and maturation of cells. Thus, the cells may be used in assays to determine the activity of media, such as conditioned media, evaluate fluids for growth factor activity, involvement with dedication of lineages, or the like.

The target OPC populations may be frozen at liquid nitrogen temperatures and stored for long periods of time, being thawed and capable of being reused. The cells will usually be stored in 7.5% DMSO and 4% HSA (human serum albumin). Once thawed, the cells may be expanded by use of growth factors or cells associated with OPC proliferation and differentiation.

Transplantation

The target OPC populations obtained from neural cell populations or neural tissue may be introduced (e.g., by transplantation) into a mammal, particularly to compensate for lost or dysfunctional oligodendrocytes. The mammal is preferably a human, canine, feline, rodent, sheep, goat, cattle, horse, pig, or non-human primate. Most preferably, the mammal is human. Since OPCs may be cultured from brain tissues from mammals of any age, including adults, it is preferable to grow neural stem cells using a mammal's own tissue for autologous transplantation. Allogeneic and xenogeneic transplantations are also possible, particularly when the transplantation site is in the brain or eye, where immunologic rejection is less severe due to the blood-brain or blood-retina barrier.

In some embodiments, the OPCs of the present embodiments are transplanted at a dose of at least on the order of greater than $1 \times 10^{20}$ total nucleated cells, or at least on the order of $10^{19}$, or $10^{18}$, or $10^{17}$, or $10^{16}$, or $10^{15}$, or $10^{14}$, or $10^{13}$, or $10^{12}$, or $10^{11}$, or $10^{10}$, or $10^{9}$, or $10^{8}$, or $10^{7}$, or $10^{6}$, or $10^{5}$ cells. In some embodiments, the OPCs of the present embodiments may be transplanted at a dose of between $1 \times 10^{6}$ to $1 \times 10^{12}$, $1 \times 10^{6}$ to $1 \times 10^{9}$, $1 \times 10^{8}$ to $1 \times 10^{10}$, $1 \times 10^{9}$ to $1 \times 10^{12}$, and $1 \times 10^{9}$ to $1 \times 10^{10}$ cells. In some embodiments, the dosage of cells is prepared in a sealed, pharmaceutical quality vial in a format that is ready to administer to a subject.

It is also that the target OPCs may be transplanted into a mammal and induced to form oligodendrocytes in vivo. Thus, target OPC populations may be expanded in culture using established methods, transplanted into the mammal, and contacted in vivo with the oligodendrocyte promoting factor to produce oligodendrocytes. Optionally, the transplanted OPCs can be expanded again in vivo by administering to the mammal any biological agents known to increase the number of OPCs.

According to some embodiments, the OPCs of the present invention are transplanted in between 1 to 5 days post passaging, preferably between 1 to 2 days past passaging. The OPCs of the present embodiments may be transplanted as clusters or disassociated cell suspensions. Engraftment data (not shown) using cells obtained in this manner are healthy and result in graft containing high number of myelinating oligodendrocytes. According to some embodiments, the OPCs of the present embodiments may be held in suspension between 10 minutes to 5 days (e.g., 30 minutes, 1 hour, 2 hours, 4 hours, 8 hours, 12 hours, 24 hours, 36 hours, 48 hours, 3 days, 4 days etc.) post passaging in a pharmaceutical quality vial in a format that is ready to administer to a subject. In some the OPCs of the present embodiments may be held in suspension at a dose of at least on the order of $1 \times 10^{20}$ total nucleated cells, or at least on the order of $10^{19}$, or $10^{18}$, or $10^{17}$, or $10^{16}$, or $10^{15}$, or $10^{14}$, or $10^{13}$, or $10^{12}$, or $10^{11}$, or $10^{10}$, or $10^{9}$, or $10^{8}$, or $10^{7}$, or $10^{6}$, or $10^{5}$ cells. In some embodiments, the OPCs of the present embodiments may be held in suspension at a dose of between $1 \times 10^{6}$ to $1 \times 10^{12}$, $1 \times 10^{6}$ to $1 \times 10^{9}$, $1 \times 10^{8}$ to $1 \times 10^{10}$, $1 \times 10^{9}$ to $1 \times 10^{12}$, and $1 \times 10^{9}$ to $1 \times 10^{10}$ cells. In some embodiments, the dosage of cells is prepared in a sealed, pharmaceutical quality vial in a format that is ready to administer to a subject.

The oligodendrocyte promoting factors or the biological agents may be administered by any suitable route established in the art, including, for example, orally, topically, rectally, vaginally, intrathecally, intravascularly, intravenously, intramuscularly, intraperitoneally, transdermally, intradermally, subcutaneously, nasally or by inhalation. The route of administration depends primarily on the nature of the agent. For example, GM-CSF is capable of crossing the blood-brain barrier, hence it can be administered systemically as well as into the brain. The preferred method of administration is injection (e.g., with a needle or a catheter) or infusion.

The target OPCs may be transplanted "naked" into patients according to conventional techniques, into the CNS as described, for example, in U.S. Pat. Nos. 5,082,670 and 5,618,531, the disclosures of which are incorporated herein by reference, or into any other suitable site in the body. In some embodiments, the OPCs are transplanted directly into the CNS. Parenchymal and intrathecal sites are contemplated. It will be appreciated that the exact location in the CNS will vary according to the disease state.

According to some embodiments, the OPCs may be allowed to aggregate prior to implantation, or may be applied directly as dissociated single cells. When using OPC aggregates, transplantation is preferably performed using small sized aggregates approximately 10-500 µm in diameter, preferably 40-50 µm in diameter. Preferably, from about 1 million cells to about 1 billion cells are transplanted. For example, a total of about 1 million, about 5 million, about 10 million, about 25 million, about 50 million, about 75 million, about 100 million, about 250 million, about 500 million, about 750 million, or about 1 billion cells are transplanted.

The OPCs are preferably introduced into the brain or spinal cord of the mammal, particularly at sites where oligodendrocytes are insufficient and/or dysfunctional, for example, around axons that have been demyelinated. In humans, areas of demyelination are generally associated with plaque like structures, which can be visualized with magnetic resonance imaging (MRI). The cells may also be transplanted into other areas of the central nervous system. One particularly useful approach is to transplant into the "mirror image" location of a target lesion in the other hemisphere, since cells are known to efficiently migrate to the corresponding location in the opposite hemisphere through the corpus callosum.

According to some embodiments, the OPCs are introduced directly to regions of the brain or spinal cord. Directed introduction of the OPCs may be carried out using any methods known in the art. Thus, according to some embodiments, the OPCs are introduced to the target brain region via injection. Preferably, the OPCs are introduced into brain regions that am heavily myelinated (rich in white matter). The firnbria is a prominent band of white matter along the medial edge of the hippocampus. White matter forms the bulk of the deep parts of the brain and the superficial parts of the spinal cord. The corpus callosum is the largest white matter structure in the brain that connects the left and right cerebral hemispheres. In some embodiments, the target brain regions include the fimbria, callosum, cerebral peduncle, internal capsule, spinal cord, brain stem, motor cortex, olfactory cortex, somatosensory cortex, anterior cingulate gyrus, the Inferior temporal lobe, and the Dorsolateral prefrontal cortex, and medulla oblongata.

Aggregates of gray matter such as the basal ganglia (caudate nucleus, putamen, globus pallidus, subthalamic nucleus, nucleus accumbens) and brain stem nuclei (red nucleus, substantia nigra, cranial nerve nuclei) are spread within the cerebral white matter. Such areas are also target brain regions. Target brain regions include, but are not limited to, the telencephalon (cerebral hemispheres, forebrain), diencephalon (thalamus, hypothalamus, epithalamus, prethalamus or subthalamus and pretectum), mesencephalon (midbrain), cerebellum, pons, and medulla oblongata. The mesencephalon includes the tectum (inferior colliculi and superior colliculi) and cerebral peduncle (midbrain tegmentum, crus cerebri, substantia nigra). The substantia nigra is part of the basal ganglia; the other parts of the basal ganglia include the striatum (caudate nucleus, putamen, and nucleus accumbens), globus pallidus, and subthalamic nucleus. Target brain regions may include the brain stem, striatum, internal capsule, caudate nucleus and putamen.

Genetic Modification of OPCs.

The OPCs of the present embodiments may be genetically modified to provide a therapeutically effective biologically active molecule. In some embodiments, the genetically modified OPCs may be transplanted or introduced to a subject in need thereof as described above.

In some embodiments, the OPCs of the present embodiments may be genetically modified to express a particular form of Myelin Proteolipid Protein (PLP), such as in the case of autologous transplant. In addition, the OPCs of the present embodiments may be genetically modified to express one or more of the following: telomerase (to prevent telomere erosion), growth factors, morphogens, enzymes, anti-apoptotic genes (e.g., sonic hedgehog, FGF2, NT3, BDNF, PDGF, IGF, NGE), arylsuphatase A (metachromatic leukodystrophy), galactosylceramidase (krabbe's), superoxide dismutase and other proteins involved in antioxidant defense, and Bcl-XL.

The OPCs described herein can be genetically engineered or modified according to known methodology. The term "genetic modification" refers to the stable or transient alteration of the genotype of a cell by intentional introduction of exogenous DNA. DNA may be synthetic, or naturally derived, and may contain genes, portions of genes, or other useful DNA sequences. The term "genetic modification" is not meant to include naturally occurring alterations such as that which occurs through natural viral activity, natural genetic recombination, or the like.

A gene of interest (i.e., a gene that encodes a biologically active molecule) can be inserted into a cloning site of a suitable expression vector by using standard techniques. These techniques are well known to those skilled in the art. See, e.g., WO 94/16718, incorporated herein by reference.

The expression vector containing the gene of interest may then be used to transfect the desired cell line. Standard transfection techniques such as calcium phosphate co-precipitation, DEAE-dextran transfection, electroporation, biolistics, or viral transfection may be utilized. Commercially available mammalian transfection kits may be purchased from e.g., Stratagene. Human adenoviral transfection may be accomplished as described in Berg et al. Exp. Cell Res., 192, pp. (1991). Similarly, lipofectamine-based transfection may be accomplished as described in Cattaneo, Mol. Brain Res., 42, pp. 161-66 (1996).

A wide variety of host/expression vector combinations may be used to express a gene encoding a biologically active molecule of interest. See, e.g., U.S. Pat. No. 5,545,723, herein incorporated by reference, for suitable cell-based production expression vectors.

Increased expression of the biologically active molecule can be achieved by increasing or amplifying the transgene copy number using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464, and European published application EP 338,841), all herein incorporated by reference.

Any expression vector known in the art may be used to express the biologically active molecule. In some embodiments, a lentivirally-derived vector may be particularly useful for the delivery of exogenous genes. Such lentiviral vectors are known in the art. In some embodiments, exogenous genes may need to be introduced into the target OPCs expression. Such genes may be under the control of a constitutive or inducible promoters to effect optimal co-expression. Exogenous DNA may be introduced to a precursor cell by viral vectors (retrovirus, modified herpes viral, herpes-viral, adenovirus, adeno-associated virus, lentivirus and the like) or direct DNA transfection (lipofection, $CaPO_4$ transfection, DEAE-dextran, electroporation, and the like).

The OPCs of the present embodiments may be genetically modified for drug screening purposes or for the purposes of detecting cells of the oligodendrocyte or OPC lineage. In some embodiments, OPCs may be genetically modified with one or more reporter genes. Such reporter genes include fluorescent proteins (e.g., green fluorescent proteins, yellow fluorescent proteins, blue fluorescent proteins, cyan fluorescent proteins, etc.), DsRed2, mCherry, tdTomato, and AmCyan1. Preferred promoters include one or more of the following promoters: MBP, CNPase, Olig2, Sox10, Plp, and PDGFR promoter.

Treatment

A number of neurologic diseases are associated with defects in myelination and in neuronal homeostasis and function. Examples of these demyelinating diseases or conditions or dysmyelinating disorders include, but are not limited to, multiple sclerosis (including the relapsing and chronic progressive forms of multiple sclerosis, acute multiple sclerosis, neuromyelitis optica (Devic,s disease)), diffuse cerebral sclerosis (including Shilder's encephalitis periaxialis diffusa and Balo's concentric sclerosis). Demyelinating diseases also include a variety of diseases wherein demyelination is caused by viral infections, vaccines, spinal cord injury, and genetic disorders. Examples of these demyelinating diseases or dysmyelinating disorders include, but are not limited to, acute disseminated encephalomyelitis (occurring after measles, chickenpox, rubella, influenza or mumps; or after rabies or smallpox vaccination), necrotizing hemorrhagic encephalitis (including hemorrhagic leukoencephalitis), and leukodystrophies (including Krabbe's globboid leukodystrophy, metachromatic leukodystrophy, adrenoleukodystrophy, adrenomyeloneuropathy, adrenomyeloneuropathy, radiation induced myelination disorders, transverse myelitits, Pelizaeus-Merzbacher disease, Canavan's disease and Alexander's disease). The demyelinating disease or dysmyelinating disorders is preferably multiple sclerosis, cerebral palsy, diffuse cerebral sclerosis, or Pelizaeus-Merzbacher disease (PMD), and, most preferably, Pelizaeus-Merzbacher disease.

The cells and methods of this invention may be useful in the treatment of various neurodegenerative diseases, demyelinating diseases and/or dysmyelinating disorders. It is contemplated that the cells will replace diseased, damaged or lost tissue in the host. Alternatively, the transplanted tissue may augment the function of the endogenous affected host tissue.

According to some embodiments, there is provided a method of enhancing oligodendrocyte production in vivo by administering the target OPCs to a mammal under conditions that result in oligodendrocyte formation. The resultant oligodendrocytes are capable of myelinating (or remyelinating) demyelinated neurons in the mammal, whereby dysmyelinating disorders and/or demyelinating diseases in the mammal can be treated or ameliorated.

According to some embodiments, there is provided a method of enhancing oligodendrocyte production in vivo by identifying and isolating target populations of OPCs, culturing the target populations of OPCs under conditions to promote their proliferations, and administering the OPCs to a mammal under conditions that result in oligodendrocyte formation. The resultant oligodendrocytes are capable of myelinating (or remyelinating) demyelinated neurons in the mammal, whereby dysmyelinating disorders and/or demyelinating diseases in the mammal can be treated or ameliorated.

According to some embodiments, there is provided a method of enhancing oligodendrocyte production in vivo by identifying and isolating target populations of OPCs, culturing the target populations of OPCs under conditions to promote their proliferations, differentiating the target populations of OPCs into oligodendrocytes, and administering the oligodendrocytes to a mammal under conditions that result in oligodendrocyte engraftment. The resultant oligodendrocytes are capable of myelinating (or remyelinating) demyelinated neurons in the mammal, whereby dysmyelinating disorders and/or demyelinating diseases in the mammal can be treated or ameliorated.

According to some embodiments, there is provided a method of enhancing oligodendrocyte production in vivo by identifying and isolating target populations of OPCs and administering target OPCs to a mammal under conditions that result in oligodendrocyte engraftment. The resultant oligodendrocytes are capable of myelinating (or remyelinating) demyelinated neurons in the mammal, whereby dysmyelinating disorders and/or demyelinating diseases in the mammal can be treated or ameliorated.

Drug Screening

The OPCs of the present invention may also be used in a method of drug screening or drug discovery. Any cell-based drug screening protocol known in the art may be used in conjunction with the OPCs of the present invention. A wide variety of assays may be used for this purpose, including toxicology testing; immunoassays for protein binding; determination of cell growth, differentiation and functional activity; production of hormones; and the like. The assays may be performed in vitro, in situ, in vivo, and ex vivo. For example, the OPCs of the present invention may be used in a drug screening method comprising the steps of a) selecting from an enriched target OPC population, b) engrafting a non-human mammal with the resulting enriched population; c) administering a test compound to the non-human mammal; and d) comparing the effect of administration of said test compound in the engrafted mammal with a control non-human mammal not administered said test compound.

According to some embodiments, the present invention provides a method of screening for compounds that affect a biological function of an enriched population of target oligodendrocyte precursor cells comprising: (a) contacting an enriched population of target oligodendrocyte precursor cells obtained by the method of claim 1 with a test compound; and (b) detecting a change in a biological function of the oligodendrocyte precursor cells. The change in biological function may include, but is not limited to, changes in one or more of the following: myelination, differentiation into oligodendrocytes, proliferation rate, cell migration, cell viability, gene expression, protein expression, protein levels in the culturing medium, dedifferentiation, growth characteristics, and/or cell morphology.

Agents are screened for biological activity by adding the agent to at least one and usually a plurality of cell samples. The change in parameters in response to the agent is measured, and the result evaluated by comparison to reference cultures, e.g. in the presence and absence of the agent, obtained with other agents, etc. The agents may be conveniently added in solution, or readily soluble form, to the medium of cells in culture. The agents may be added in a flow-through system, as a stream, intermittent or continuous, or alternatively, by adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells. Thus, antibodies can be modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantization of nucleic acids, especially messenger RNAs, is also of interest as a parameter. These can be measured by hybridization techniques that depend on the sequence of nucleic acid nucleotides. Techniques include polymerase chain reaction methods as well as gene array techniques.

Encapsulation

Any encapsulation protocol known in the art may be used with the OPCs of the present invention. The OPCs of the present invention may be encapsulated and used to deliver biologically active molecules, according to known encapsulation technologies, including microencapsulation (see, e.g., U.S. Pat. Nos. 4,352,883; 4,353,888; and 5,084,350, incorporated herein by reference), macroencapsulation (see, e.g., U.S. Pat. Nos. 5,284,761, 5,158,881, 4,976,859 and 4,968,733 and published PCT patent applications WO 92/19195, WO 95/05452, each incorporated herein by reference).

If the OPCs are encapsulated, macroencapsulation as described in U.S. Pat. Nos. 5,284,761; 5,158,881; 4,976,859; 4,968,733; 5,800,828 and published PCT patent application WO 95/05452, each incorporated herein by reference is preferred. Cell number in the devices can be varied. Preferably each device contains between $10^3$-$10^9$ cells, most preferably $10^5$-$10^7$ cells. A large number of macroencapsulation devices may be implanted in the patient; preferably between one to 10 devices.

The following examples are illustrative, but not limiting, of the methods and compositions of the present invention. Other suitable modifications and adaptations of the variety of conditions and parameters normally encountered in therapy and that are obvious to those skilled in the art are within the spirit and scope of the embodiments.

Example 1: Selection of PDGFR Positive Cells

Fetal brain (16-20 weeks of gestation) was enzymatically treated with a combination of collagenase/hyaluronidase and trypsin to generate a single cell suspension. Cells were resuspended in Hank's balanced salt solution containing 1 mM Sodium Pyruvate and 0.1% human serum albumin (staining buffer) and stained with the CD133 antibody. CD133$^+$ cells were aseptically sorted using a BD Vantage flow cytometer, under enrichment mode. CD133$^+$ enriched fraction was centrifuged, ressuspended in staining buffer and incubated with a 1:100 dilution of rabbit anti PDGFRα polyclonal antibody (IgG) for 2 hours at 4° C. After two rinses in staining buffer, PDGFRα labeled cells were incubated for polyclonal goat anti-rabbit IgG-FITC antibody (Caltag). PDGFRα positive (F1TC labeled) cells were aseptically sorted using a BD Vantage flow cytometer, under purity mode. Sorted cells were cultured on poly-L-ornithine, laminin and fibronectin coated culture flasks in DMEM medium supplemented with B27, N2, NAC, L-Glutamine, Na Pyruvate, FGF2, PDGF-AA and NT3 (complete medium), with or without IGF1. Cell passaging was achieved by mild trypsin treatment and re-plating in the same medium.

An alternative method used for the purification of PDGFRα positive cells is to stain total brain cells (with or without enrichment for CD133) with the mouse monoclonal antibody 1:50 PDGFRα-PE (Pharmingen) for 2 h at 4° C., followed by purity aseptic sorting using a BD Aria flow cytometer.

Example 2: Selection of CD105 Negative Cells

The use of CD105 cells as a selection marker is based on the present inventors discovery that some cultures of purified PDGFRα$^+$ cells expand at a much faster rate then others. Such accelerated growth was generally accompanied by the appearance of a cell type with a morphology distinct from that of oligodendrocyte progenitors. Based on the morphology and accelerated growth in culture, it is likely that these cells are PDGFRα$^+$ fibroblasts; the growth advantage of fibroblasts in FGF2 containing media is well documented. Moreover, apart from exhausting mitogens, fibroblasts may also negatively condition the culture medium, affecting the growth kinetics and the differentiation process of oligodendrocyte progenitors into oligodendrocytes, both in vitro and in vivo. The presence of these fibroblastic cells therefore reduces the efficiency in obtaining an expanded culture of oligodendrocyte progenitors.

It is desirable to define a more pure and homogeneous oligodendrocyte progenitor population, especially in the case when contaminating cells have growth advantage. Therefore a search was initiated for cell surface markers expressed specifically in fibroblasts that could be used to distinguish them from PDGFRα+ oligodendrocyte progenitors. A panel of antibodies was used to stain cultures containing a mixture of fibroblasts and oligodendrocytes. The results showed that the monoclonal antibody to CD105, which recognizes the glycoprotein endoglin, is a useful reagent to subdivide the PDGFRα+ population into two subpopulations: PDGFRα+CD105+ (fibroblasts) and PDGFRα+CD105− (oligodendrocyte progenitors).

The sorting protocol for the isolation of fetal derived human oligodendrocyte progenitors includes two antibodies, CD105-APC and PDGFRα-PE. Various cell lots have been generated using this two antibody protocol. The results indicate that these cell lots have similar growth characteristics and oligodendrocyte differentiation potential. Further, the appearance of fibroblasts is not observed in these cultures, up to passage 15, the highest passage tested. The results demonstrate that CD105 is a useful negative selection marker for use in obtaining a desirable population of oligodendrocyte progenitors.

Example 3: Media for Proliferating OPCs

Proliferation medium was prepared with the following components in the indicated concentrations: Component Final Concentration DMEM, glutamine (Invitrogen, cat#25030-081) 2 mM, Na Pyruvate (Sigma, cat# S8636), 1 mM, NAC (Sigma, cat# A9165), 1 mM, N2 supplement (Invitrogen, cat#17502-048; containing transferrin, insulin, putrescine, selenium and progesterone), B27 supplement (Invitrogen, cat #17504-044), 20 ng/ml human bFGF (Biosource, cat# PHG0024), 20 ng/ml PDGF-AA (Peprotech, cat#100-13A) 10 ng/ml NT3 (Peprotech, cat#450-03), 100 ng/ml IGF1 (Peprotech, cat #AF-100-11).

Example 4: Differentiation of OPCs

In a first differentiation protocol, proliferating OPCs are induced to differentiate by physical removal or exhaustion of the growth factor mitogens from the cell culture with addition of triiodothyronine (T3).

The staining protocol for oligodendrocytes was as follows:

O4 Staining for Oligodendrocytes. Cells are incubated with primary antibodies to O4 (hybridoma supernatant, mouse monoclonal; used at 1:2) for 30 min at room temperature. Cells are washed once with 0.1 M PBS, pH 7.4. Cells are fixed for 20 min at room temperature with ice-cold 4% paraformaldehyde. Cells are washed twice for 5 min with 0.1 M PBS, pH 7.4. Cells preparations are blocked for 30 min at room temperature in 10% horse serum ("HS") diluted in 0.1M PBS, pH 7.4. Cells are incubated with secondary antibodies (donkey anti mouse IgG/Alexa488 used at 1:500, (Invitrogen, Cat# A21202); or goat anti mouse IgM/Alexa 488, (Invitrogen, Cat# A21042) diluted in 1% HS for 1hr at room temperature in the dark. Preparations are washed twice for 5 min with 0.1 M PBS in the dark. Preparations are mounted onto slides face down with mounting medium (Vectashield Mounting Medium, Vector Laboratories, cat# H-1000) or left on culture wells for quantification and qualification of staining and stored at 4° C.

In some instances stain with Hoechst (a nuclear stain) may be used as follows. Cells prepared as above are washed with Hoechst solution (diluted 1:10,000 in 0.1% saponin, Sigma, Cat#54521). Cells are incubated in Hoechst solution for 5 min at room temperature, followed by 2 washes in 0.1M PBS.

Example 5: Differentiation of OPCs

In a second differentiation protocol, the OPCs are induced to differentiate by removal of the growth factor mitogens and provision of 1% serum. This differentiation protocol produces cell cultures highly enriched in oligodendrocytes.

In a third differentiation protocol, the OPCs are induced to differentiate by removal of the growth factor mitogens and provision of 30 nM T3 (Sigma, cat# T5516). This differentiation protocol produces cell cultures highly enriched in oligodendrocytes.

Example 6: Encapsulation

If the OPCs are encapsulated, then the following procedure may be used: The hollow fibers are fabricated from a polyether sulfone (PES) with an outside diameter of 720 m and a wall thickness of a 100 m (AKZO-Nobel Wuppertal, Germany). These fibers are described in U.S. Pat. Nos. 4,976,859 and 4,968,733, herein incorporated by reference. The fiber may be chosen for its molecular weight cutoff. A PES#5 membrane which has a MWCO of about 280 kd is occasionally used. In other studies, a PES#8 membrane which has a MWCO of about 90 kd may be used.

The devices typically comprise: 1) a semipermeable poly (ether sulfone) hollow fiber membrane fabricated by AKZO Nobel Faser AG; 2) a hub membrane segment; 3) a light cured methacrylate (LCM) resin leading end; and 4) a silicone tether.

The semipermeable membrane used typically has the following characteristics: Internal Diameter 500+30 m Wall Thickness 100+15 m Force at Break 100+15 cN Elongation at Break 44+10% Hydraulic Permeability 63+8 (ml/min m² mmHg) nMWCO (dextrans) 280+20 kd.

The components of the device are commercially available. The LCM glue is available from Ablestik Laboratories (Newark, Del.); Luxtrak Adhesives LCM23 and LCM24). The tether material is available from Specialty Silicone Fabricators (Robles, Calif.). The tether dimensions are 0.79 mm ODX0.43 mm IDXlength 202 mm. The morphology of the device is as follows: The inner surface has a permselective skin. The wall has an open cell foam structure. The outer surface has an open structure, with pores up to 1.5 m occupying 30+5% of the outer surface.

Fiber material is first cut into 5 cm long segments and the distal extremity of each segment sealed with a photopolymerized acrylic glue (LCM-25, ICI). Following sterilization with ethylene oxide and outgassing, the fiber segments are loaded with a suspension of between $10^4$-$10^7$ cells, either in a liquid medium, or a hydrogel matrix (e.g., a collagen solution (Zyderm™), alginate, agarose or chitosan) via a Hamilton syringe and a 25 gauge needle through an attached injection port. The proximal end of the capsule is sealed with the same acrylic glue.

A silicone tether (Specialty Silicone Fabrication, Taunton, Ma.) (ID: 690 m; OD: 1.25 mm) is placed over the proximal end of the fiber allowing easy manipulation and retrieval of the device.

Example 7: Transplantation of OPCs

Target OPCs may be transplanted into rodent brain to assess graft viability, integration, phenotypic fate of the grafted cells, as well as behavioral changes associated with grafted cells in healthy animals.

Transplantation is performed according to standard techniques. For example, adult rats are anesthetized with sodium pentobarbitol (45 mg/kg, i.p.) and positioned in a Kopf stereotaxic instrument. A midline incision is made in the scalp and a hole drilled for the injection of cells. Rats receive implants of target OPCs into the striatum using a glass capillary attached to a 10 µl Hamilton syringe. Each animal receives a total of about 250,000-500,000 cells in a total volume of 2 µl. Cells are transplanted 1-2 days after passaging and the cell suspension is made up of undifferentiated OPC clusters of 5-20 cells. Following implantation, the skin is sutured closed.

Example 8: Transplantation of OPCs into Rodent Models of Dysmyelinating Disease Target OPCs may be transplanted into rodent brain to assess graft viability, integration, phenotypic fate of the grafted cells, as well as behavioral changes associated with grafted cells in lesioned or diseased animals.

Transplantation is performed according to standard techniques. For example, newborn end rats or jimpy mice are anesthetized by hypothermia and positioned in a Kopf stereotaxic instrument. A midline incision is made in the scalp and a hole drilled for the injection of cells. Animals receive implants of target OPCs into the corpus callosum, fimbria, cerebellar peduncle and/or spinal cord using a glass capillary attached to a 10 µl Hamilton syringe. Each animal receives a total of about 300,000-600,000 cells in a total volume of 6 µl. Cells are transplanted immediately or 1-2 days after passaging and the cell suspension is made up of undifferentiated single OPCs or clusters of 5-20 cells. Following implantation, the skin is sutured or staple closed.

Alternatively, newborn or juvenile shiverer mice are anesthetized by hypothermia or isofluorane and positioned in a Kopf stereotaxic instrument. A midline incision is made in the scalp and a hole drilled for the injection of cells. Mice receive implants of target OPCs into the corpus callosum, fimbria, cerebellar peduncle and/or spinal cord using a glass capillary attached to a 10 µl Hamilton syringe. Each animal receives a total of about 300,000-600,000 cells in a total volume of 6 µl. Cells are transplanted immediately or 1-2 days after passaging and the cell suspension is made up of undifferentiated single OPCs or clusters of 5-20 cells. Following implantation, the skin is sutured or staple closed.

Example 9: Treatment of Neurodegenerative Disease Using Progeny of Target OPCs In Vitro Target OPCs are obtained from fetal brain tissue following routine suction abortion which is collected into a sterile collection apparatus. A 2×4×1 mm piece of tissue is dissected and dissociated as in Examples 1 or 2. Target OPCs are then proliferated. The target OPC progeny are used for neurotransplantation into a blood-group matched host with a neurodegenerative disease. Surgery is performed using a BRW computed tomographic (CT) stereotaxic guide. The patient is given local anesthesia suppiemencea with intravenously administered midazolam. The patient undergoes CT scanning to establish the coordinates of the region to receive the transplant. The injection cannula consists of a 17-gauge stainless steel outer cannula with a 19-gauge inner stylet. This is inserted into the brain to the correct coordinates, then removed and replaced with a 19-gauge infusion cannula that has been preloaded with 30 µl of tissue suspension. The cells are slowly infused at a rate of about 3 µl/min as the cannula is withdrawn. Multiple stereotactic needle passes are made throughout the area of interest, approximately 4 mm apart. The patient is examined by CT scan postoperatively for hemorrhage or edema. Neurological evaluations are performed at various post-operative intervals, as well as PET scans to determine metabolic activity of the implanted cells.

Example 10: Genetic Modification of Target OPC Progeny Using Calcium Phosphate Transfection Target OPC progeny are propagated as described herein. The cells are then transfected using a calcium phosphate transfection technique. For standard calcium phosphate transfection, the cells are mechanically dissociated into a single cell suspension and plated on tissue culture-treated dishes at 50% confluence (50,000-75,000 cells/cm$^2$) and allowed to attach overnight.

The modified calcium phosphate transfection procedure is performed as follows: DNA (15-25 µg) in sterile TE buffer (10 mM Tris, 0.25 mM EDTA, pH 7.5) diluted to 440 µl with TE, and 60 µl of 2M CaCl$^2$ (pH to 5.8 with 1M HEPES buffer) is added to the DNA/TE buffer. A total of 500 µl of 2×HeBS (HEPES-Buffered saline; 275 mM NaCl, 10 mM KCl, 1.4 mM Na$_2$ HPO$_4$, 12 mM dextrose, 40 mM HEPES buffer powder, pH 6.92) is added dropwise to this mix. The mixture is allowed to stand at room temperature for 20 minutes. The cells are washed briefly with 1×HeBS and 1 ml of the calcium phosphate precipitated DNA solution is added to each plate, and the cells are incubated at 37° for 20 minutes. Following this incubation, 10 mls of complete medium is added to the cells, and the plates are placed in an incubator (37° C., 9.5% CO$_2$) for an additional 3-6 hours. The DNA and the medium are removed by aspiration at the end of the incubation period, and the cells are washed 3 times with complete growth medium and then returned to the incubator.

Example 11: Genetic Modification of Target OPCs Using Viral Vectors

Target OPCs are proliferated as described herein and then infected with lentiviral vectors containing genes of interest in addition to a report gene such as GFP (green fluorescence protein). Lentivirus suspensions am added to the culture medium where OPCs are proliferated and incubated for 24 hours. After 24 h, the culture medium is removed and replaced with fresh medium and the OPCs are cultured for another 3 days. Cells are collected and centrifuged and cells expressing the gene of interest are sorted by flow cytometry. Positive cells are returned to the proliferative medium.

The transduced OPC progeny are transplanted into a rodent or human patient using the procedures described in the previous Examples.

Example 12: Transplantation of OPCs into Rodent Models of Spinal Cord Injury Target OPCs may be transplanted into rodent spinal cord to assess graft viability, integration, phenotypic fate of the grafted cells, as well as behavioral changes associated with grafted cells in spinal cord lesioned animals.

Animals receive a laminectomy at vertebral level T9. Animals then receive a 50-kilodyne (kd) contusion spinal cord injury using an Infinite Horizon Impactor (Precision Systems and Instrumentation, Lexington, Ky.). Seven days after spinal cord injury, mice are tested using the Basso, Beattie, and Bresnahan (BBB) rating scale and randomized to receive OPCs or vehicle control. Cells are injected bilaterally anterior and posterior to the epicenter of the lesion using a beveled grass micropipette affixed to a nanoinjector device. Each animal receives 50,000 to 80,000 cells.

Example 13: Transplantation of OPCs into Rodent Models of MS

Myelin oligodendrocyte glycoprotein (MOG)-induced murine experimental autoimmune encephalomyelitis (EAE) is a widely accepted model for studying the clinical and pathological features of multiple sclerosis.

Transplantation is performed according to standard techniques. For example, adult animals affected by MOG-induced EAE are anesthetized using isoflurane gas and positioned in a Kopf stereotaxic instrument. A midline incision is made in the scalp and a hole drilled for the injection of cells. Animals receive implants of target OPCs into the corpus callosum, fimbria, cerebellar peduncle, lateral ventricular space and/or spinal cord using a glass capillary attached to a 10 μl Hamilton syringe. Each animal receives a total of about 300,000-600,000 cells in a total volume of 6 μl. Cells are transplanted immediately or 1-2 days after passaging and the cell suspension is made up of undifferentiated single OPCs or clusters of 5-20 cells. Following implantation, the skin is sutured or staple closed.

Example 14: Characterization of the Engraftment Ability of Expanded PDGFR$^+$CD105$^-$ Oligodendrocyte Progenitor (OPC) Population In order to determine whether FACS-isolated, in vitro expanded oligodendrocyte progenitor cells survive, migrate and are capable of in vivo myelination, a series of transplantation studies were conducted using the shiverer mouse, a rodent model of dysmyelination. The shiverer mouse contains a naturally occurring deletion of a large portion of the mbp gene which results in incomplete CNS myelin formation. In order to avoid xenogenic rejection of human cells, the shiverer mice were backcrossed to the immunodeficient NOD-Scid mouse. Engraftment of oligodendrocyte progenitors was studied in two different Shiverer/Scid age groups: as juveniles (P21-P30) and as neonates (P0-P1). Shiverer/Scid mice have a relatively short lifespan of around 8 weeks and therefore the longest post transplantation time point studied was about 8 weeks in the case of neonatal injections and 5 weeks for juvenile injections.

Oligodendrocyte progenitors are grown as a monolayer. In order to prepare cells for transplantation, OPCs were lifted off the flasks using trypsin, following a protocol similar to that used to passage OPCs. Cells were then exposed to trypsin inhibitor to stop the proteolytic digestion, washed twice in culture medium and ressuspended in ex-vivo medium containing the antioxidant NAC (1 mM) at a final density of 1E5 cells/μl.

The ability for OPCs to be held in a suspension culture format for at least one day post trypsin treatment was tested. This 1-day hold period in suspension could be advantageous for 3 reasons: 1) would allow cells to recover from a potentially damaging enzyme treatment prior to transplantation and/or cryopreservation; 2) it would introduce more flexibility in animal surgery scheduling and 3) would make shipment of ready-to-transplant OPCs to an off-site location (laboratory or clinic) possible. Finally, and given the potential application of OPCs for clinical application, the engraftment ability and myelination potential of OPCs after cryopreservation was tested with positive results.

Example 15: Transplantation

Juvenile or neonatal shiverer/Scid mice were placed in a stereotaxic frame and 1 μl of OPC suspension was injected into 2-3 brain locations, bilaterally (4-6 total injections/mouse). Injections targeted the corpus callosum, fimbria and the cerebellar peduncle (see FIG. 1), regions of the brain that are heavily myelinated (rich in white matter) in myelin-competent animals but severely hypomyelinated in the shiverer/scid mouse. Mice were sacrificed at different time points, up to 8 weeks, and their brains analyzed for the presence of human cells using the monoclonal antibody SC121 and for the presence of human derived oligodendrocytes, capable of myelinating mouse axons, using an MBP antibody. Because shiverer mice have a mutation that deletes most of the mbp gene, MBP protein is not produced by mouse oligodendrocytes and therefore any MBP detected by the anti-MBP antibody is of human origin.

Table 15-1—Summary of Engraftment Data Obtained from 4 OPC Lines Derived from 4 Different Donor Tissues.

| Donor ID, age | Passage tested | Shiverer age group | Total # transplanted Shi/Scid mice | Presence of donor cells SC121$^+$ | Myelin production M1313$^+$ |
|---|---|---|---|---|---|
| 2657, 18 wks | 3, 13 & 14 | Juvenile | 10 | 10/10 | 10/10 |
| 2703, 18 wks | 6, 9, 14, 15 & 16 | Juvenile & Neonates | 4 juv + 15 neo | 19/19 | 19/19 |
| 2710, 18 wks | 2 | Neonates | 2 | 2/2 | 2/2 |
| 2711, 18 wks | 4, 6, 11 & 12 | Neonates | 16 | 16/16 | 16/16 |

Figure 2:
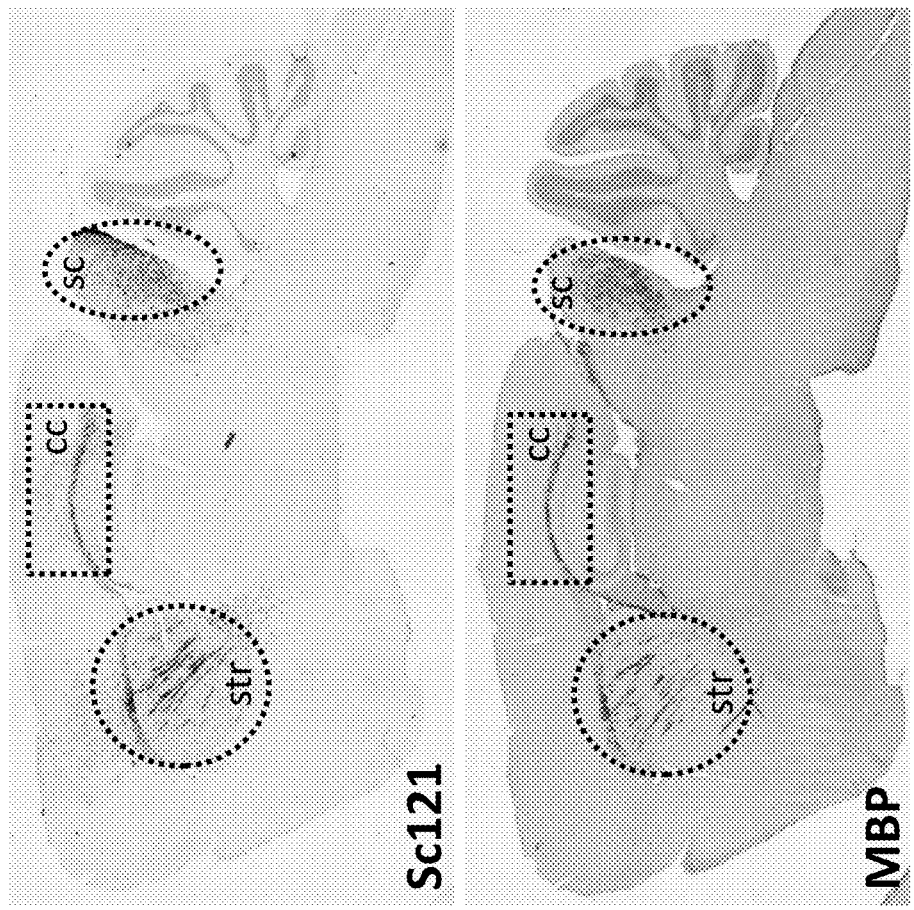
FIG. 2. Example of OPC engraftment in the neonatal shiverer/scid mouse. Top panel shows sc121 staining, highlighting all donor derived cells. The bottom panel shows MBP staining in a serial sister section. Dotted regions of interest have been drawn to indicate the areas of engraftment and of corresponding myelination. In this example, the superior colliculus was targeted. Cell line information: FBr 2711, P6, 8 weeks post transplant. Abbreviations used: str, striatum; cc, corpus callosum; sc, superior colliculus.

All juvenile and neonatal animals injected with OPCs contained human cells (as determined by SC121 staining) at all ages tested. When stained for MBP, all animals also demonstrated positive staining (see FIG. 2 for one example of SC121 and MBP staining in serial sections).

Figure 3:
FIG. 3. Example of MBP-GFP transduced OPC engraftment in the neonatal shiverer/scid mouse. Top panel shows GFP staining, highlighting donor derived cells that are actively transcribing the mbp gene. The bottom panel shows MBP staining in a serial sister section. Dotted regions of interest have been drawn around the cerebellum and are shown in the panels on the light at higher magnification. Note that there is a digital misalignment of the cerebellum in the MBP panel as indicated by the white arrows. Cell line information: FBr 2703, P6, 8 weeks post transplant. Abbreviations used: cb, cerebellum.

The possibility of genetically modifying OPCs with lentiviral vectors was also tested. As a proof of concept, we used a lentiviral vector expressing the reporter gene GFP (green fluorescence protein) under the control of the MBP promoter. This allows for direct visualization (antibody staining free) of the OPCs that are actively transcribing the MBP gene (bright green cells) and that have the morphology of mature myelinating oligodendrocytes (multiple processes with cable like morphology, aligned with axonal bundles). FIG. 3 shows one example of a shiverer/scid mouse transplanted with MBP-GFP OPCs, sacrificed at 8 weeks post transplantation.

The in vivo study showed that neonates and juvenile shiverer mice are appropriate models for testing engraftment and myelination ability of expanded OPCs. Major differences in the engraftment quality between neonate and juvenile shiverer/scid mice were not observed.

The in vivo study showed that engraftment of OPCs and myelination were not significantly affected by passage number; for instance, in neonates that were injected with donor 2703, there was no qualitative difference in the total number of human cells and the extent of myelination, suggesting that potency (ability to engraft and to myelinate) does not diminish with passage up to passage 16, the longest passage number tested.

The in vivo study showed that when the potency of freshly passaged (never frozen) OPCs is compared with that of previously cryopreserved OPCs at the same or similar passage, there were no major qualitative differences in engraftment and myelination. Although only neonatal animals were transplanted with previously cryopreserved cells, we do not expect a different outcome in juvenile animals. This result indicates that OPC cultures can be cryoprotected without any detectable loss in potency. Similarly, there is no loss of potency (engraftment or myelination ability) due to the one-day hold period, suggesting that this protocol can be used to facilitate OPC culture transfers to off site locations in a ready-to-use format.

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs.

What is claimed is:

1. A method of producing a population enriched for oligodendrocyte precursor cells comprising:
    (a) contacting neural or neural derived cells comprising one or more multipotent central nervous system stem cell with an antibody that specifically binds to PDGFRα; and
    (b) selecting said neural or neural derived cells that are PDGFRα$^{hi}$, wherein the selected cells are enriched for oligodendrocyte precursor cells as compared with the neural or neural derived cells.
2. The method of claim 1, wherein said neural or neural derived cells are obtained from a neurosphere culture or an adherent culture.
3. The method of claim 1, wherein the method further comprises the step of eliminating those cells that are PDGFRα$^{lo/med}$.
4. The method of claim 1, wherein the method further comprises the step of eliminating cells that are CD105$^+$.
5. The method of claim 4, wherein the oligodendrocyte precursor cells are PSA-NCAM$^{lo/-}$.
6. The method of claim 4, wherein the oligodendrocyte precursor cells are A2B5$^{lo/-}$.
7. The method of claim 4, wherein the oligodendrocyte precursor cells are CD133$^+$.
8. The method of claim 7, wherein the oligodendrocyte precursor cells are A2B5$^{lo/-}$.
9. The method of claim 8, wherein the oligodendrocyte precursor cells are PSA-NCAM$^{lo/-}$.
10. The method of claim 1, wherein the oligodendrocyte precursor cells are CD105$^-$.
11. The method of claim 1, wherein the oligodendrocyte precursor cells are PSA-NCAM$^{lo/-}$.
12. The method of claim 1, wherein the oligodendrocyte precursor cells are A2B5$^{lo/-}$.
13. The method of claim 1, wherein the oligodendrocyte precursor cells are CD133$^+$.

* * * * *